United States Patent [19]

Platzek et al.

[11] Patent Number: 6,019,959
[45] Date of Patent: Feb. 1, 2000

[54] OLIGOMERIC COMPOUNDS THAT CONTAIN PERFLUOROALKYL, PROCESS FOR THEIR PRODUCTION, AND THEIR USE IN NMR DIAGNOSIS

[75] Inventors: Johannes Platzek; Ulrich Niedballa; Bernd Raduchel; Wolfgang Schlecker; Hanns-Joachim Weinmann; Thomas Frenzel, all of Berlin; Bernd Misselwitz, Glienicke; Wolfgang Ebert, Mahlow, all of Germany

[73] Assignee: Schering Aktiengesellschaft, Germany

[21] Appl. No.: 09/106,146

[22] Filed: Jun. 29, 1998

Related U.S. Application Data

[60] Provisional application No. 60/054,417, Jul. 31, 1997.

[51] Int. Cl.[7] .......................... A61K 51/00; A61B 5/055; C07F 15/00; C07F 19/00
[52] U.S. Cl. .................... 424/9.36; 424/1.65; 424/9.361; 424/9.363; 540/470; 540/474; 534/14; 564/191; 564/198
[58] Field of Search ..................................... 540/465, 474, 540/470; 424/1.65, 9.36, 9.363; 534/14; 564/191, 198

[56] References Cited

U.S. PATENT DOCUMENTS 4,885,363 12/1989 Tweedle et al. ..................... 540/465
5,690,909 11/1997 Platzek et al. ........................... 424/363
5,712,389 1/1998 Meyer et al. ............................. 540/474
5,820,849 10/1998 Schmitt-Willich et al. ........... 424/9.36
5,834,456 11/1998 Kiefer et al. ............................. 514/186
5,853,699 12/1998 Maier et al. .......................... 424/9.363

OTHER PUBLICATIONS

19603033 Jul. 24, 1997 DERWENT (Abstract).
19608278 Aug. 28, 1997 DERWENT (Abstract).
19521945 Dec. 19, 1996 DERWENT (Abstract).

*Primary Examiner*—Mukund J. Shah
*Assistant Examiner*—Pavanaram K Sripada
*Attorney, Agent, or Firm*—Millen, White, Zelane, & Branigan, P.C.

[57] ABSTRACT

Oligomeric compounds that contain perfluoroalkyl of general formula I $$A\text{—}R^F \qquad (I)$$

in which

A is a molecule portion that contains 2–6 metal complexes that are connected directly or via a linker to a nitrogen atom of an annular skeleton chain, and $R^F$ is a perfluorinated, straight-chain or branched carbon chain with formula $-C_nF_{2n}E$, in which E represents a terminal fluorine, chlorine, bromine, iodine, or hydrogen atom and n stands for numbers 4–30, are valuable compounds for diagnosis, especially as in-vivo contrast media.

20 Claims, No Drawings

OLIGOMERIC COMPOUNDS THAT CONTAIN PERFLUOROALKYL, PROCESS FOR THEIR PRODUCTION, AND THEIR USE IN NMR DIAGNOSIS

Provisional application No. 60/054,417 filed Jul. 31, 1997.

The invention relates to the subjects that are characterized in the claims, i.e., new oligomeric compounds that contain perfluoroalkyl, pharmaceutical agents that contain these compounds, a process for their production, and their use as contrast media in $^1$H-NMR diagnosis and spectroscopy, x-ray diagnosis, and radiodiagnosis, as well as radiotherapeutic agents.

Today nuclear-magnetic resonance (NMR) is a medical diagnostic method that is used extensively for in-vivo imaging, with which the body's vessels and bodily tissue (including tumors) can be visualized by measuring the magnetic properties of protons in the body's water. To accomplish this, e.g., contrast media are used that produce contrast enhancement in the resulting images or that make these images readable by influencing certain NMR parameters of the body's protons (e.g., relaxation times $T^1$ and $T^2$). Complexes of paramagnetic ions, such as, e.g., gadolinium-containing complexes (e.g., Magnevist®) are used mainly because of the effect that the paramagnetic ions have on the shortening of the relaxation times. A measure of the shortening of the relaxation time is relaxivity, which is indicated in $mM^{-1} \cdot sec^{-1}$.

Paramagnetic ions, such as, e.g., $Gd^{3+}$, $Mn^{2+}$, $Cr^{3+}$, $Fe^{3+}$ and $Cu^{2+}$ cannot be administered in free form as solutions since they are highly toxic. To make these ions suitable for in-vivo use, they are generally complexed; this was first described in EP 0 071 564 A1 (complexing with aminopolycarboxylic acids, e.g., with diethylenetriamine-pentaacetic acid [DTPA]). The di—N-methylglucamine salt of the Gd-DTPA complex is known under the name magnevist®) and is used, i.a., to diagnose tumors in the human brain and in the kidneys.

The meglumine salt of Gd-DOTA (Gadolinium(III) complex of 1,4,7,10-tetracarboxymethyl-1,4,7,10-tetraazacyclododecane) that is described in French Patent 25 39 996 is another contrast medium that has also proven very useful in nuclear spin tomography and was registered under the name Dotarem®.

These contrast media cannot be used satisfactorily for all applications, however. Thus, the contrast media that are now used in clinical practice for the modern imaging processes of nuclear spin tomography (MRI) and computer tomography (CT), such as, e.g., Magnevest®, Pro Hance®, Ultravist®, and Omniscan® are dispersed throughout the entire extracellular space of the body (in the intravascular space and in the interstitium).

Especially for visualizing vessels, however, contrast media are desirable that, upon administration into the vascular space (vessel space), are also exclusively dispersed in the latter and thus label it (so-called blood-pool agents).

An attempt was made to solve these problems by using complexing agents that are bonded to macromolecules or biomolecules. This approach has had only very limited success thus far.

Thus, for example, the number of paramagnetic centers in the complexes, which are described in EP 0 088 695 A1 and EP 0 150 844 A1, is not sufficient for satisfactory imaging.

If the number of required metal ions is increased by repeatedly introducing complexing units into a macromolecular biomolecule, this is associated with an intolerable negative impact on the affinity and/or specificity of this biomolecule [J. Nucl. Med. 24, 1158 (1983)].

Macromolecular contrast media for angiography, such as albumin-Gd-DTPA, are described in Radiology 1987; 162: 205. 24 hours after intravenous injection in rats, however, albumin-Gd-DTPA shows a concentration in the liver tissue that is almost 30% of the dose. In addition, only 20% of the dose is eliminated within 24 hours.

The macromolecule polylysine-Gd-DTPA (EP 0 233 619 A1) can also be used as a blood-pool agent. For production reasons, however, this compound consists of a mixture of molecules of different sizes. In excretion tests in rats, it was shown that this macromolecule is excreted through the kidneys unaltered by glomerular filtration. For synthesis reasons, however, polylysine-Gd-DTPA also contains macromolecules that are so large that they cannot pass through the renal capillaries with glomerular filtration and thus remain in the body.

Macromolecular contrast media based on carbohydrates, e.g., dextran, have also been described (EP 0 326 226 A1). The drawback of these compounds lies in the fact that the latter generally carry only about 5% of the signal-enhancing paramagnetic cation.

The object of the invention was therefore to make available new contrast media that do not have the above-mentioned drawbacks and show a higher proton relaxivity, especially in $^1$H-NMR diagnosis and thus make it possible to reduce the dose when the signal intensity is increased. The contrast media also are to be stable and well-tolerated and mainly have organ-specific properties, whereby on the one hand their retention in the organs that are to be examined is to be sufficient to obtain the number of images that is necessary for an unambiguous diagnosis at a lower dosage, but on the other hand, as quick and as complete excretion of the metals from the body as possible is then to be ensured.

The object of the invention is achieved with the oligomeric compounds that contain perfluoroalkyl of general formula I:

in which

A is a molecule portion that contains 2–6 metal complexes that are connected directly or via a linker to a nitrogen atom of an annular skeleton chain, and $R^F$ is a perfluorinated, straight-chain or branched carbon chain with formula —$C_nF_{2n}$E, in which E represents a terminal fluorine, chlorine, bromine, iodine, or hydrogen atom and n stands for numbers 4–30, characterized in that molecule portion A has the following structure:

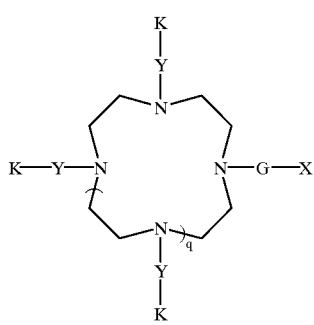

whereby q is a number 0, 1, 2 or 3,

K stands for a complexing agent or metal complex or their salts of organic and/or inorganic bases or amino acids or amino acid amides, X is a direct bond to the perfluoroalkyl group, a phenylene group, or a $C_1$–$C_{10}$ alkylene chain, which optionally contains 1–15 oxygen atoms, 1–5 sulfur atoms, 1–10 carbonyl groups, 1–10 (NR) groups, 1–2 $NRSO_2$ groups, 1–10 CONR groups, 1 piperidine group, 1–3 $SO_2$ groups, 1–2 phenylene groups or optionally is substituted by 1–3 radicals $R^F$, in which R stands for a hydrogen atom, a phenyl, benzyl or a $C_1$–$C_{15}$ alkyl group, which optionally contains 1–2 NHCO groups, 1–2 CO groups, 1–5 oxygen atoms, and optionally is substituted by 1–5 hydroxy radicals, 1–5 methoxy radicals, 1–3 carboxy radicals, 1–3 $R^F$ radicals, Y is a direct bond or a chain of general formula II or III:

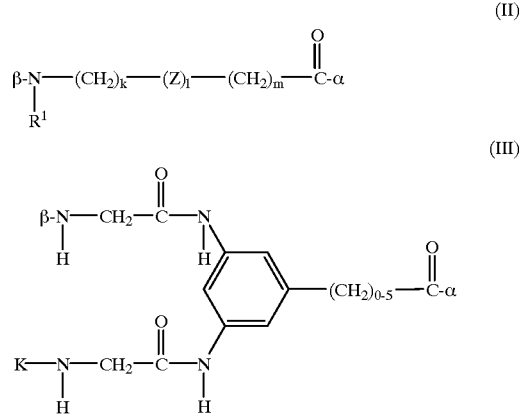

in which

R$^1$ is a hydrogen atom, a phenyl group, a benzyl group or a $C_1$–$C_7$ alkyl group, which optionally is substituted with a carboxy group, a methoxy group, or a hydroxy group, Z is a direct bond, a polyglycol ether group with up to 5 glycol units, or a molecule portion of general formula IV

in which R$^2$ is a $C_1$–$C_7$ carboxylic acid, a phenyl group, a benzyl group, or a —(CH$_2$)$_{1-5}$—NH—K group, α represents the bond to the nitrogen atom of the skeleton chain, and β is the bond to the complexing agent or metal complex K, and in which variables k and m stand for natural numbers between 0 and 10 and 1 stands for 0 or 1, and whereby G is a CO or $SO_2$ group.

These compounds have a surprisingly high proton relaxivity in comparison to the commercially available $^1$H-NMR contrast media Magnevist®, Dotarem®, Omniscan®, and Pro Hancec® (here, the values for the $T^1$-relaxivity are between 3.5–4.9 [mM$^{-1}$·sec$^{-1}$, 39° C., 0.47 T], in this regard, see Table 1 before Example 28).

In addition, the compounds according to the invention are extremely well suited for detecting and localizing vascular diseases since, when administered into the intravascular space, they are dispersed exclusively in the latter. With the aid of nuclear spin tomography, the compounds according to the invention make it possible to delimit tissue that is well supplied with blood from tissue that is poorly supplied with blood and thus to diagnose an ischemia. Due to its anemia, infarcted tissue can also be delimited from surrounding healthy or ischemic tissue when the contrast media according to the invention are used. This is of particular importance if, e.g., the point is to distinguish a myocardial infarction from an ischemia.

Compared to the macromolecular compounds that were previously used as blood-pool agents, such as, for example, Gd-DTPA-polylysine, the compounds according to the invention also show a higher $T^1$-relaxivity and are thus distinguished by an increased signal intensity in NMR imaging. Since, in addition, they have extended retention in the blood space, they can also be administered at relatively small doses (of, e.g., ≦50 μmol of Gd/kg of body weight). In particular, however, the compounds according to the invention are eliminated quickly and as completely as possible from the body.

It was also shown that the compounds according to the invention are concentrated in areas with increased vascular permeability, such as, e.g., in tumors; they make it possible to make statements about tissue perfusion and offer a way to determine the blood volume in tissues, to shorten the relaxation times or densities of the blood selectively, and to graphically display the permeability of the blood vessels. Such physiological data cannot be obtained by the use of extracellular contrast media, such as, e.g., Gd-DTPA (Magnevist®). These considerations also give rise to their uses in the modern imaging processes nuclear spin tomography and computer tomography: more specific diagnoses of malignant tumors, early therapy monitoring in cytostatic, antiphlogistic, or vaso-dilatative therapy, early detection of underperfused fields (e.g., in the myocardium), angiography in the case of vascular diseases, and detection and diagnosis of (sterile or infectious) inflammations.

In addition, it was shown that the compounds of this invention are suitable not only as blood-pool agents, but can also be used extremely well as lymph-specific NMR contrast media (lymphographic agents).

The visualization of the lymph nodes is of central importance for early detection of metastatic attack in cancer patients. The contrast media according to the invention make it possible to distinguish small metastases in non-enlarged lymph nodes (<2 cm) of lymph node hyperplasias without malignant attack. In this case, the contrast media can be administered intravascularly or interstitially/intracutaneously. Interstitial/intracutaneous administration has the advantage that the substance is transported directly from the scattering focus (e.g., primary tumor) by the corresponding lymph tracts into the potential regional lymph node stations in question. Likewise, with a small dose, a high concentration of the contrast medium in the lymph nodes can be achieved.

The compounds according to the invention meet all of the requirements that are imposed by contrast media in indirect NMR lymphography: good local compatibility, quick removal from the injection site, quick and as complete an elimination as possible from the entire organism. They also show a high concentration over several lymph node stations and thus allow relevant diagnostic assessments. Thus, in the guinea pig model, a high concentration over several lymph node stations (popliteal, inguinal, iliac) after s.c. administration (2.5–10 μmol/kg of body weight, injection in the interdigital spaces of the hind paws) was shown. In especially suitable cases, gadolinium concentrations of, respectively, ≧200 or ≧300 μmol/l were thus obtained in the second (inguinal) and third (iliac) stations. Lymph node concentrations up to 1,000 μmol/l can usually be obtained with the compounds according to the invention.

In humans, the compounds according to the invention can be injected locally (either subcutaneously or directly percutaneously into the tissue of interest). Several injection sites (weals) with respective injection volumes of 0.2 to 1 ml that are grouped around the area to be studied (e.g., tumors), are possible. In this case, the total volume injected should never exceed 5 ml. This means that a metal concentration of 75–100 mmol/l must be present in the formulation, so that a potential clinical dose of 5–10 μmol/kg of body weight can be administered with this volume. The administration site depends on whether a certain lymph outflow field from the tissue that corresponds to it is to be specifically dyed (e.g., in the case of gynecological or rectal tumors) or whether the unknown outflow field of a certain lesion (ergo the area of a possible therapeutic intervention, e.g., in melanoma or breast cancer) is to be visualized.

For MR imaging in normal lymph node tissue, where the concentration of the compound takes place, gadolinium concentrations of at least 40 μmol/l and at most 2,500 μmol/l are required. Imaging can (depending on the injection site and tissue) be carried out after 30 minutes or up to 4–6 hours after injection of the compounds according to the invention. Since mainly the $T^1$-relaxation times of the protons of the water of the lymph node tissue are influenced with the compounds of gadolinium complexes according to the invention, $T^1$-weighted sequences are best able to detect an NMR enhancement of the lymph node stations. Since lymph nodes are very frequently embedded in fat tissue and the latter has a very high signal intensity in such sequences, fat-suppressed measuring methods are offered. Paramagnetic gadolinium complexes in connection with fat-suppressed $T^1$-weighted measuring sequences have the great advantage, compared to formulations of superparamagnetic iron oxide particles, that they allow NMR images with higher spatial resolution, with fewer distortion artifacts (due to susceptibility artifacts), and with shorter imaging time.

Since positive labeling of the lymph nodes is carried out (i.e., signal increase), NMR pictures without contrast media are also no longer absolutely necessary for comparison, and the overall examination time per patient can be shortened.

Of the new oligomeric compounds that contain perfluoroalkyl of general formula I according to the invention, those with q in the meaning of number 1 are preferred.

As a molecule portion X in the meaning of an alkylene chain, the following structures can be mentioned by way of example;

Υ-(CH$_2$)$_{0-15}$-δ,

Υ-⟨phenyl⟩-(OCH$_2$CH$_2$)$_{1-5}$-δ,

Υ-⟨phenyl⟩-(CH$_2$)$_{0-10}$-δ,

Υ-(CH$_2$)$_{1-9}$—CO—NR—CH$_2$CH$_2$-δ,

Υ-(CH$_2$)$_{1-15}$—S—CH$_2$CH$_2$-δ,

Υ-(CH$_2$)$_{1-10}$—NR—SO$_2$-δ,

Υ-(CH$_2$)$_{1-10}$—OCH$_2$CH$_2$-δ,

-continued

Υ-CH$_2$NH(COCH$_2$NH)$_{1-5}$—CO—CH$_2$—OCH$_2$CH$_2$-δ,

Υ-(CH$_2$)$_{1-10}$—N(COR)—CH$_2$CH$_2$-δ,

Υ-(CH$_2$)$_{1-9}$—CO—N(CH$_2$CH$_2$NHCOCH$_2$OCH$_2$CH$_2$R$^F$),
        |
        CH$_2$CH$_2$NHCOCH$_2$OCH$_2$CH$_2$-δ

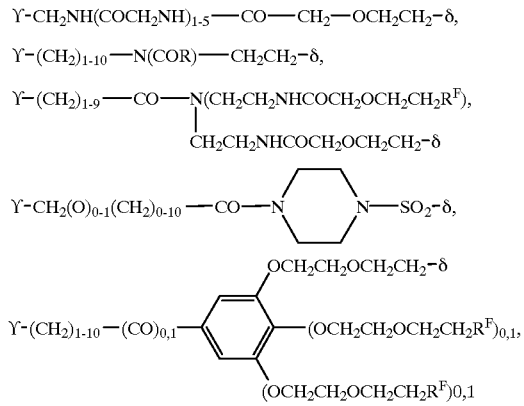

whereby γ binds to G and δ binds to R$^F$, and R stands for a hydrogen atom, a phenyl group, benzyl group or a C$_1$–C$_{15}$ alkyl group, which optionally contains 1–2 NHCO groups, 1–2 CO groups, 1–5 oxygen atoms, and optionally is substituted by 1–5 hydroxy radicals, 1–5 methoxy radicals, 1–3 carboxy radicals or 1–3 R$^F$ radicals.

Preferred molecule portions X are alkylene chains, which contain 1–10 CH$_2$CH$_2$O groups or 1–5 COCH$_2$NH groups.

Especially preferred for X are the direct bond and the following structures:

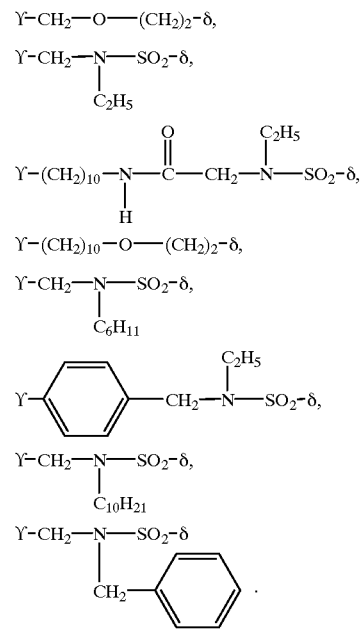

As a molecule portion Y, the following structures can be mentioned:

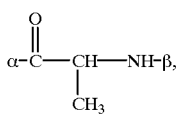

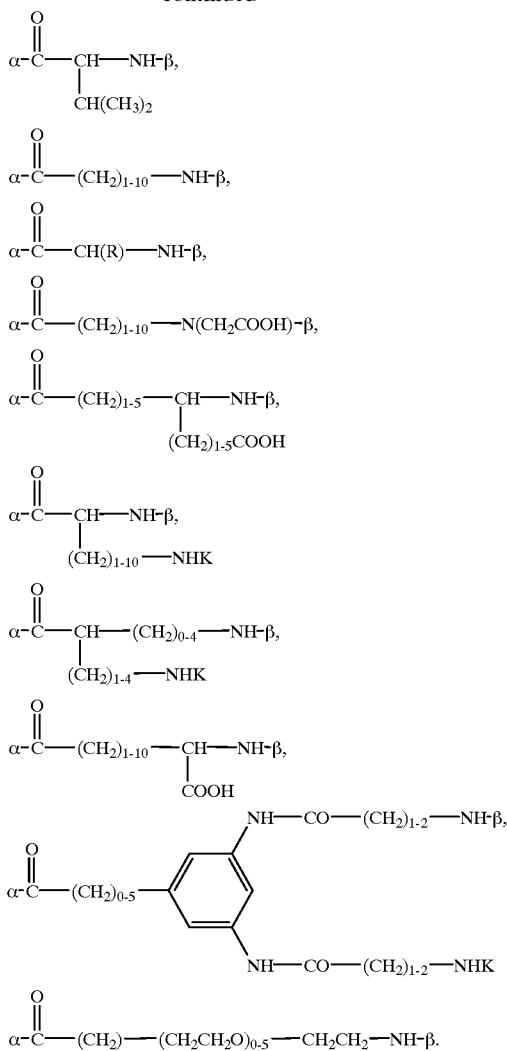

Preferred molecule portions Y are the direct bond and the following structures:

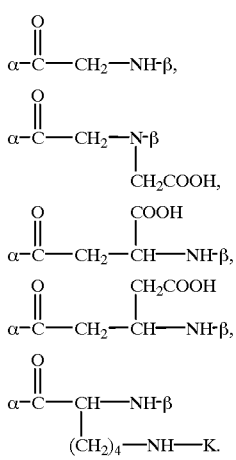

The complexing agents or metal complexes have the following structures:

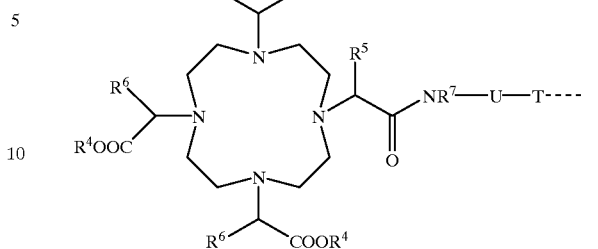

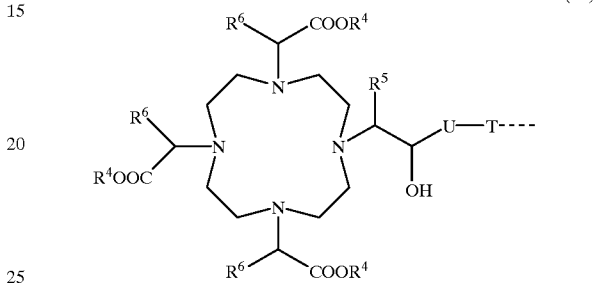

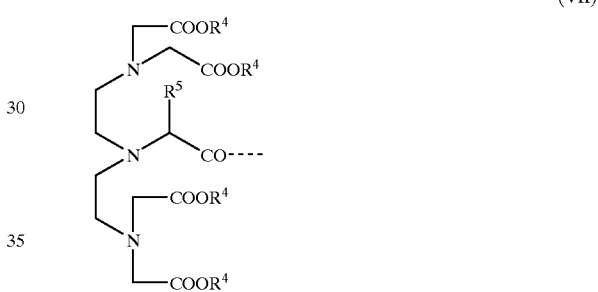

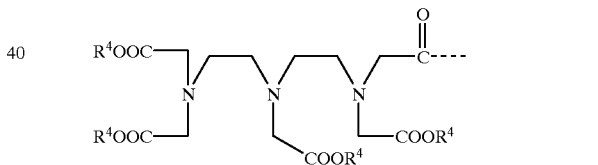

whereby
- $R^4$, independently of one another, are a hydrogen atom or a metal ion equivalent of the elements of atomic numbers 20–32, 37–39, 42–44, 49 or 57–83,
- $R^5$ is a hydrogen atom or a straight-chain, branched, saturated or unsaturated $C_1$–$C_{30}$ alkyl chain, which optionally is substituted by 1–5 hydroxy groups, 1–3 carboxy groups or 1 phenyl group(s) and/or optionally is interrupted by 1–10 oxygen atoms, 1 phenylene group or 1 phenylenoxy group,
- $R^6$ is a hydrogen atom, a straight-chain or branched $C_1$–$C_7$ alkyl radical, a phenyl or benzyl radical,
- $R^7$ is a hydrogen atom, a methyl or ethyl group, which optionally is substituted by a hydroxy or carboxy group,
- U is a straight-chain, branched, saturated or unsaturated $C_1$–$C_{20}$ alkylene group that optionally contains 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atoms, and/or optionally is substituted by 1–5 hydroxy, 1–2 mercapto, 1–5 oxo, 1–5 thioxo, 1–3 carboxy, 1–5 carboxyalkyl, 1–5 ester and/or 1–3 amino groups, whereby the optionally contained phenylene groups can be substituted by 1–2 carboxy, 1–2 sulfone or 1–2 hydroxy groups, T stands for a —CO—β, —NHCO—β or —NHCS—β group, whereby β represents the binding site to Y.

As preferred substituents $R^5$, there can be mentioned:

the hydrogen atom, the methyl, ethyl, propyl, isopropyl, benzyl, phenyl, —CH$_2$CH$_2$OH, —CH$_2$OH, —CH$_2$—COOH, —COOH, —CH$_2$CHOHCH$_2$OH, —CH$_2$O—CH$_2$CH$_2$OCH$_3$, —CH$_2$OCH$_3$, —CH$_2$—O—C$_6$H$_4$—COOH group.

As preferred substituents $R^6$, there can be mentioned:

the hydrogen atom, the methyl, ethyl, propyl, isopropyl, benzyl and phenyl group.

As preferred substituents $R^7$, there can be mentioned:

the hydrogen atom, the methyl, ethyl, —CH$_2$CH$_2$OH, —CH$_2$—COOH group.

The $C_1$–$C_{10}$ alkylene chain that stands for U preferably contains the following groups:

—CH$_2$NHCO—, —NHCOCH$_2$O—, —NHCOCH$_2$OC$_6$H$_4$—, —N(CH$_2$CO$_2$H)—, —CH$_2$OCH$_2$—, —NHCOCH$_2$C$_6$H$_4$—, —NHCSNHC$_6$H$_4$—, —CH$_2$OC$_6$H$_4$—, —CH$_2$CH$_2$O—, and/or is substituted by the groups —COOH, —CH$_2$COOH.

As examples of U, the following groups can be indicated:

—CH$_2$—, —CH$_2$CH$_2$—, —CH$_2$CH$_2$CH$_2$—, —C$_6$H$_4$—, —C$_6$H$_{10}$—, —CH$_2$C$_6$H$_4$—,

—CH$_2$NHCOCH$_2$CH(CH$_2$CO$_2$H)—C$_6$H$_4$—,

—CH$_2$NHCOCH$_2$OCH$_2$—,

—CH$_2$NHCOCH$_2$C$_6$H$_4$—,

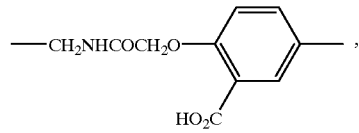

—CH$_2$NHCSNH—C$_6$H$_4$—CH(CH$_2$COOH)CH$_2$—,

—CH$_2$OC$_6$H$_4$—N(CH$_2$COOH)CH$_2$—,

—CH$_2$NHCOCH$_2$O(CH$_2$CH$_2$O)$_4$—C$_6$H$_4$—,

—CH$_2$O—C$_6$H$_4$—,

—CH$_2$CH$_2$—O—CH$_2$CH$_2$—, —CH$_2$CH$_2$—O—CH$_2$CH$_2$—O—CH$_2$CH$_2$—,

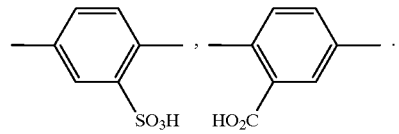

As examples of K, the following structures can be indicated:

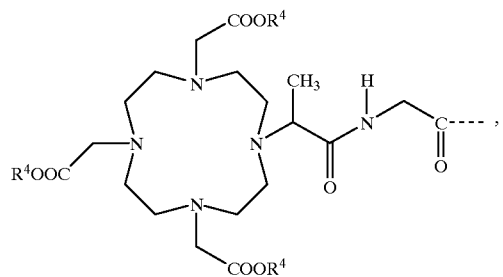

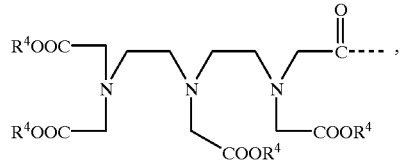

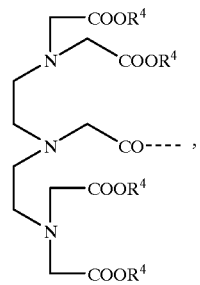

-continued

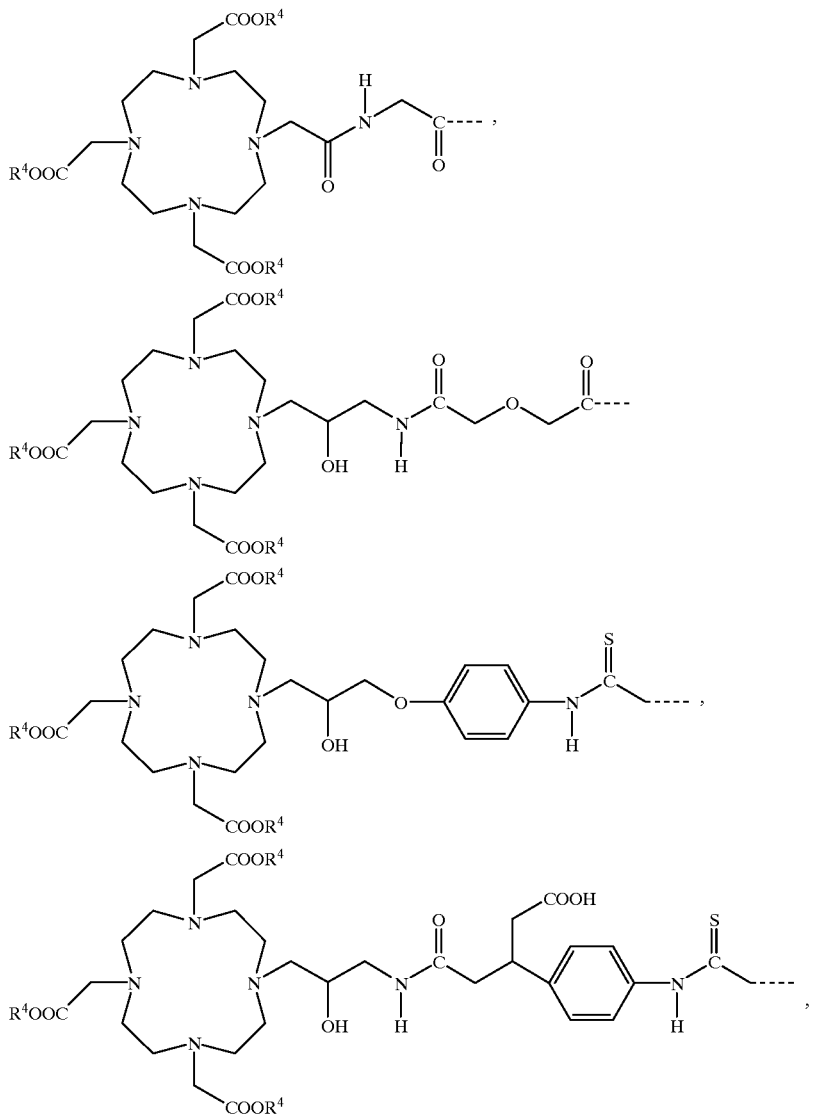

whereby the first five mentioned above are preferred.

$R^F$ stands for a —$C_nF_{2n}$E chain, in which E stands for a terminal F, Cl, Br, I or H atom, preferably for an F atom and n stands for numbers 4–30, preferably 6–12. Preferred $R^F$ chains are the following:

—$C_6F_{13}$, —$C_8F_{17}$, —$C_{10}F_{21}$ and —$C_{12}F_{25}$.

If the agent according to the invention is intended for use in NMR diagnosis, the central ion of the complex salt must be paramagnetic. These are especially the divalent and trivalent ions of the elements of atomic numbers 21–29, 42, 44 and 58–70. Suitable ions are, for example, the chromium (III), iron(II), cobalt(II), nickel(II), copper(II), praseodymium(III), neodymium(III), samarium(III) and ytterbium(III) ion. Because of their very strong magnetic moment, the gadolinium (III), terbium(III), dysprosium(III), holmium(III), erbium(III), manganese(II) and iron(III) ions are especially preferred.

If the agent according to the invention is intended for use in diagnostic radiology, the central ion must be derived from an element of a higher atomic number to achieve adequate absorption of x-rays. It has been found that for this purpose, diagnostic agents that contain a physiologically compatible complex salt with central ions of elements of atomic numbers between 21–29, 39, 42, 44, 57–83 are suitable; these are, for example, the lanthanum(III) ion and the above-mentioned ions of the lanthanide series.

The residual acidic hydrogen atoms, i.e., those that have not been substituted by the central ion, can optionally be replaced completely or partially by cations of inorganic and/or organic bases, amino acids or amino acid amides.

Suitable inorganic cations are, for example, the lithium ion, the potassium ion, the calcium ion, the magnesium ion and especially the sodium ion. Suitable cations of organic bases are, i.a., those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, arginine and ornithine and the amides of otherwise acidic or neutral amino acids.

The production of the compounds of general formula I according to the invention is carried out in that compounds of general formula I'

$$A'\text{—}R^F \qquad (I')$$

in which A' stands for a radical

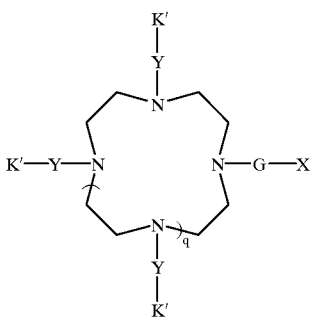

and K' stands for K with $R^4$ in the meaning of a hydrogen atom or a carboxy protective group, are reacted after cleavage of the optionally present protective groups in a way that is known in the art with at least one metal oxide or metal salt of an element of atomic numbers 20–32, 37–39, 42–44, 49 or 57–83 and optionally then still present acidic hydrogen atoms in the complex compounds that are thus obtained are substituted completely or partially by cations of inorganic and/or organic bases, amino acids or amino acid amides.

If K stands for a tetraazamacrocycle, the synthesis of the compounds according to the invention can also be carried out in such a way that a compound of general formula I"

(I")

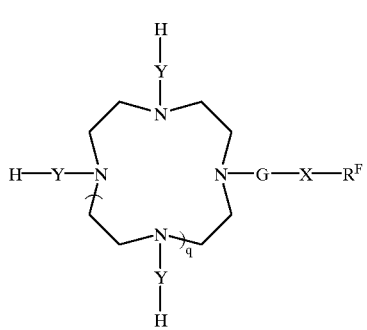

is reacted with a complex V' or VI', (V')

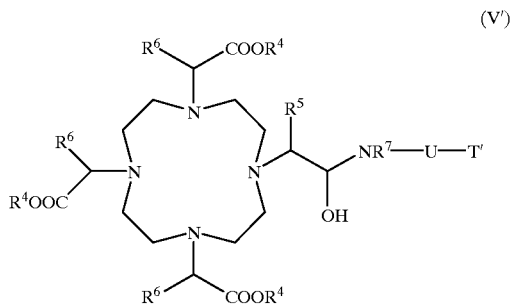

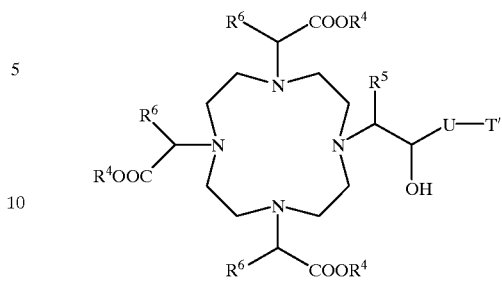

(VI')

whereby T' stands for a —C*O, —COOH, —N=C=O or —N=C=S group and —C*O stands for an activated carboxyl group, provided that at least two (in the case of divalent metals) or three (in the case of trivalent metals) of substituents $R^4$ stand for a metal ion equivalent of the above-mentioned elements, and that optionally other carboxyl groups are present in the form of their salts with inorganic and/or organic bases, amino acids or amino acid amides.

As examples of an activated carbonyl group C*O, anhydride, p-nitrophenylester, N-hydroxysuccinimide ester, pentafluorophenyl ester and acid chloride can be mentioned.

If $R^4$ stands for an acid protective group, lower alkyl, aryl and aralkyl groups, for example, the methyl, ethyl, propyl, butyl, phenyl, benzyl, diphenylmethyl, triphenylmethyl, bis-(p-nitrophenyl)-methyl group and trialkylsilyl groups are suitable.

The optionally desired cleavage of the protective groups is carried out according to the processes that are known to one skilled in the art (see, e.g., E. Wünsch, Methoden der Org. Chemie [Methods of Organic Chemistry], Houben-Weyl, Volume XV/1, 4th Edition 1974, p. 315), for example by hydrolysis, hydrogenolysis, alkaline saponification of esters in aqueous alcoholic solution at temperatures of 0° C. to 50° C., acid saponification with mineral acids or in the case of tert-butyl esters with the aid of trifluoroacetic acid.

The introduction of the desired metal ions is carried out in the way in which it was disclosed in, e.g., German Laid-Open Specification 34 01 052, by the metal oxide or a metal salt (for example, the nitrate, acetate, carbonate, chloride or sulfate) of the element of atomic numbers 20–32, 37–39, 42–44, 57–83 being dissolved or suspended in water and/or a lower alcohol (such as methanol, ethanol or isopropanol) and reacted with the solution or suspension of the equivalent amount of complexing ligand and then, if desired, present acidic hydrogen atoms of the acid groups being substituted by cations of inorganic and/or organic bases, amino acids or amino acid amides.

The introduction of the desired metal ions can be carried out both in the stage of general formula I' or before the coupling of structural parts K, i.e., in the stage of the production of complexes V' or VI'.

In this case, neutralization is carried out with the aid of inorganic bases (for example, hydroxides, carbonates or bicarbonates) of, for example, sodium, potassium, lithium, magnesium or calcium and/or organic bases, such as, i.a., primary, secondary and tertiary amines, such as, for example, ethanolamine, morpholine, glucamine, N-methylglucamine and N,N-dimethylglucamine, as well as basic amino acids, such as, for example, lysine, arginine and ornithine or amides of originally neutral or acidic amino acids, such as, for example, glycinamide.

For the production of neutral complex compounds, enough of the desired bases can be added to, for example, the acidic complex salts in aqueous solution or suspension so that the neutral point is reached. The solution that is obtained can then be evaporated to the dry state in a vacuum. It is often advantageous to precipitate the neutral salts that are formed by adding water-miscible solvents, such as, for example, lower alcohols (methanol, ethanol, isopropanol, etc.), lower ketones (acetone, etc.), polar ethers (tetrahydrofuran, dioxane, 1,2-dimethoxyethane, etc.) and thus to obtain easily isolated and readily purified crystallizates. It has proven especially advantageous to add the desired base as early as during the complexing of the reaction mixture and thus to save a process step.

If the acidic complex compounds contain several free acid groups, it is often suitable to produce neutral mixed salts that contain both inorganic and organic cations as counterions.

This can be done by, for example, the complexing ligands in aqueous suspension or solution being reacted with the oxide or salt of the element that yields the central ion and half of the quantity of an organic base that is required for neutralization, the formed complex salt being isolated, optionally purified and then mixed with the required quantity of inorganic base for complete neutralization. The sequence in which the base is added can also be reversed.

The purification of the complex that is thus obtained is carried out, optionally after setting the pH to 6 or 8, preferably about 7, by adding an acid or base preferably by ultrafiltration with membranes of suitable pore size (e.g., Amicon® YMI, Amicon® YM3), gel filtration on, e.g., suitable Sephadex® gels or by HPLC on silica gel or reverse-phase material.

In the case of neutral complex compounds, it is often advantageous to pour the oligomeric complexes over an anion exchanger, for example IRA 67 (OH⁻ form) and optionally in addition over a cation exchanger, for example IRC 50 (H⁺ form) to separate ionic components.

The synthesis of the compounds of general formula I', i.e., the linkage of complexing agents to compounds of formula I", is carried out just like the coupling of the metal complexes of general formula K' to the compounds of general formula I" analogously to methods that are known in the literature, as they are described in, e.g., U.S. Pat. No. 5,135,737, H. Takalo et al., Bioconjugate Chem. 1994, 5, 278; EP 0430863; EP 0331616; WO 96/01655; EP 0271 180; U.S. Pat. No. 5,364,613; WO 95/17451 and WO 96/02669. It is performed in solvents such as, e.g., water, methylene chloride, acetonitrile, chloroform, DMSO, pyridine, ethanol/water, ethanol/acetonitrile, dioxane, DMF, THF, lower alcohols, tetramethylurea, N-methylpyrrolidone, polyethylene glycols, 1,2-dimethoxyethane, dimethylacetamide, formamide, 1,2-dichloroethane or—if possible—their mixtures with water at temperatures of −10° C. to 100° C., preferably 0 to 50° C., especially preferably at room temperatures within 5 minutes to 72 hours, preferably 1 to 24 hours, especially preferably 1 to 14 hours, optionally with the addition of an organic or inorganic base, such as, e.g., aromatic or aliphatic amines, alkali hydroxides or alkaline-earth hydroxides, -carbonates or bicarbonates and quaternary ammonium hydroxides. By way of example, triethylamine, diisopropyl-N-ethylamine (Hünig base), N-methylmorpholine, tributylamine, tetramethylethylenediamine, pyridine, lutedine, 2,4,6-trimethylpyridine, 4-dimethylaminopyridine, N-methylimidazole, tetramethylguanidine, DBU, lithium, sodium, potassium, calcium, magnesium, barium hydroxide, -carbonate, -bicarbonate can be mentioned. The reaction can also be carried out in the buffer solutions that are known to one skilled in the art, preferably at pH 8 to 11, especially preferably at pH 8.5 to 9. The observance of pH value range is preferably done using a pH-stat.

If the coupling is carried out with a metal complex, preferably dimethylsulfoxide is used as a solvent. In this case, it has proven advantageous to use salts, such as, e.g., lithium chloride, sodium bromide, lithium bromide and lithium iodide as solubility-improving additives.

If the coupling is carried out in an in-situ-activated carboxyl group, coupling reagents that are known to one skilled in the art, such as, e.g., DCCI, EEDQ, Staab reagent, BOP, PyBOP, TBTU, TDBTU, HBTU (see, e.g., Fournic-Zaluski et al., J. Med. Chem. 1996, 39, 2596; Houben-Weyl, Volume XV/2, Part II, 1974; Y. M. Angell et al., Tetrahedron Letters 1994, 35, 5981; L. A. Carpino et al., J. Chem. Soc. Commun. 1994, 201; H.-O. Kim et al., Tetrahedron Letters 1995, 36, 6013; D. Papaioannou et al., Tetrahedron Letters, 1995, 36, 5187, G. Stemple et al., Bioorg. Med. Letters 1996, 6, 55) can be used.

The activated complexes or complexing agents V', VI', VII', VIII', and VIII'a that are used as starting substances

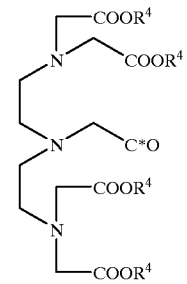

(VII')

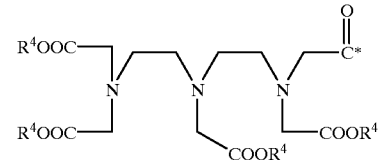

(VIII')

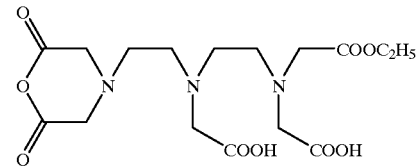

(VIII'a)

are known in the literature or can be obtained analogously to methods that are known in the literature:

VIII' and VIII'a, see, e.g., EP 263 059,

VII', see, e.g., DE 19507822, DE 19580858, DE 19507819,

V' and VI', see, e.g., U.S. Pat. No. 5,053,503, WO 96/02669, WO 96/01655, EP 0430863, EP 255471, U.S. Pat. No. 5,277,895, EP 0232751, U.S. Pat. No. 4,885,363.

The starting substances of general formula I" are obtained from compounds of general formula IA

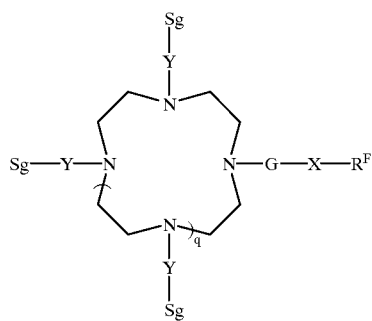

(IA)

in which Sg stands for an amino protective group.

As amino protective groups, the benzyloxycarbonyl, tert-butoxycarbonyl, trifluoroacetyl, fluorenylmethoxycarbonyl, benzyl, formyl, 4-methoxybenzyl-, 2,2,2-trichloroethoxycarbonyl, phthaloyl, 1,2-oxazoline, tosyl, dithiasuccinoyl, allyloxycarbonyl, sulfate, pent-4-enecarbonyl, 2-chloroacetoxymethyl (or -ethyl) benzoyl, tetrachlorophthaloyl, alkyloxycarbonyl groups that are familiar to one skilled in the art, can be mentioned [Th. W. Greene, P. G. M. Wuts, Protective Groups in Organic Syntheses, 2nd Ed., John Wiley and Sons (1991), pp. 309–385; E. Meinjohanns et al., J. Chem. Soc. Pekin Trans 1, 1995, 405; U. Ellensik et al., Carbohydrate Research 280, 1996, 251; R. Madsen et al., J. Org. Chem. 60, 1995, 7920; R. R. Schmidt, Tetrahedron Letters 1995, 5343].

The cleavage of the protective groups is carried out according to the processes that are known to one skilled in the art (see, e.g., E. Wunsch, Methoden der Org. Chemie, Houben-Weyl, Volume XV/1, 4th edition 1974, p. 315), for example by hydrolysis, hydrogenolysis, alkaline saponification of the esters with alkali in aqueous-alcoholic solution at temperatures of 0° C. to 50° C., acidic saponification with mineral acids or in the case of Boc groups with the aid of trifluoroacetic acid.

The production of the protected macrocycles of general formula IA can be carried out by acylation of compounds of general formula IB

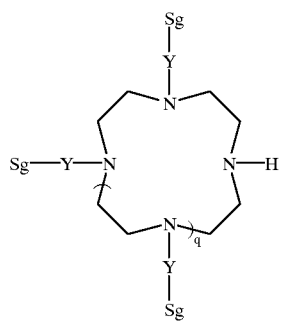

(IB)

with a substrate of general formula IC that introduces the desired substituent

Nu—G—X—R$^F$ (IC)

in which Nu stands for a nucleofuge.

Advantageously used as nucleofuges are the radicals:

F, Cl, Br, I, —OTs, —OMs, OH,

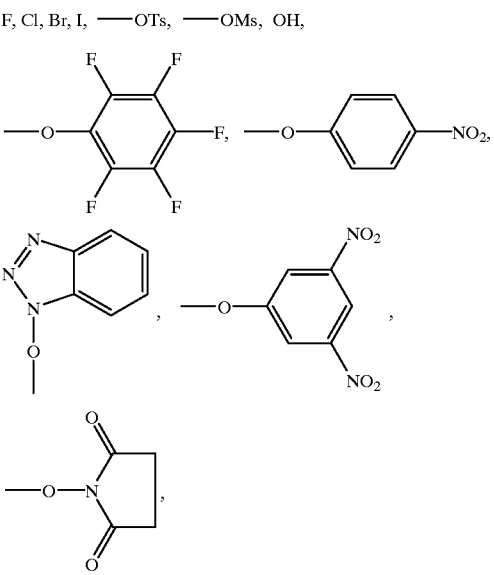

The reaction is carried out in a mixture of water and organic solvents such as isopropanol, ethanol, methanol, butanol, dioxane, tetrahydrofuran, dimethylformamide, dimethylacetamide, formamide or dichloromethane. Ternary mixtures that consist of water, isopropanol and dichloromethane are preferred.

The reaction is carried out at a temperature interval of between −10° C.–100° C., preferably between 0° C.–30° C.

As acid traps, inorganic and organic bases, such as triethylamine, pyridine, N-methylmorpholine, diisopropylethylamine, dimethylaminopyridine, alkali and alkaline-earth hydroxides, their carbonates or bicarbonates, such as lithium hydroxide, sodium hydroxide, potassium hydroxide, sodium carbonate, sodium bicarbonate, and potassium bicarbonate are used.

If Nu stands for an OH group, coupling reagents that are known to one skilled in the art, such as, e.g., DCCI, EEDQ, Staab reagent, BOP, PyBOP, TBTU, TDBTU, HBTU (see, e.g., Fournic-Zaluski et al., J. Med. Chem. 1996, 39, 2596; Houben-Weyl, Volume XV/2, Part II, 1974; Y. M. Angell et al., Tetrahedron Letters 1994, 35, 5981; L. A. Carpino et al., J. Chem. Soc. Commun. 1994, 201; H.-O. Kim et al., Tetrahedron Letters 1995, 36, 6013; D. Papaioannou et al., Tetrahedron Letters, 1995, 36, 5187, G. Stemple et al., Bioorg. Med. Letters 1996, 6, 55; can be used.

The production of compounds IB that are required as educts for the above-mentioned acylation reaction is described in DE-OS 19549286.

The synthesis of the compounds of general formula IC is carried out according to the methods that are known to one skilled in the art and is adequately described in the examples.

Another possible synthesis of macrocycles of general formula IA consists in the fact that compounds of general formula IE

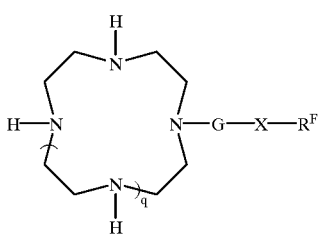

are reacted with compounds of general formula ID that are known in the literature Nu—Y—Sg    (ID)

in a way that is known to one skilled in the art, as described in the reaction of IB with IC.

The above-mentioned compounds of general formula IE are obtained by cleavage of amino protective groups from compounds of general formula IF,

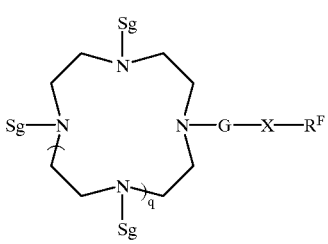

which are accessible from the compounds of general formula IG that are known in the literature.

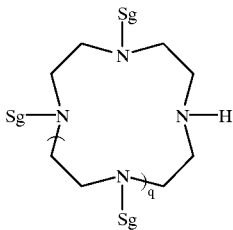

The latter can be obtained by acylation with substrates of general formula IC analogously to the above-described reaction of IB with IC.

The production of the pharmaceutical agents according to the invention is carried out in a way that is known in the art by the complex compounds according to the invention—optionally with the addition of the additives that are commonly used in galenicals—being suspended or dissolved in aqueous medium and then the suspension or solution optionally being sterilized. Suitable additives are, for example, physiologically harmless buffers (such as, for example, tromethamine), additives of complexing agents or weak complexes (such as, for example, diethylenetriaminepentaacetic acid or the Ca-oligomer complexes that correspond to the metal complexes according to the invention) or—if necessary—electrolytes, such as, for example, sodium chloride or—if necessary—antioxidants such as, for example, ascorbic acid.

If suspensions or solutions of the agents according to the invention in water or physiological salt solution are desired for enteral or parenteral administration or other purposes, they are mixed with one or more adjuvant(s) that are commonly used in galenicals [for example, methyl cellulose, lactose, mannitol] and/or surfactant(s) [for example, lecithins, Tween®, Myrj®] and/or flavoring substance(s) for taste correction [for example, ethereal oils].

In principle, it is also possible to produce the pharmaceutical agents according to the invention without isolating the complexes. In any case, special care must be taken to perform the chelation so that the complexes according to the invention are virtually free of noncomplexed metal ions that have a toxic action.

This can be ensured, for example, with the aid of color indicators such as xylenol orange by control titrations during the production process. The invention therefore also relates to a process for the production of complex compounds and their salts. As a final precaution, there remains purification of the isolated complex.

The pharmaceutical agents according to the invention preferably contain 0.1 μmol–1 mol/l of the complex and are generally dosed in amounts of 0.0001–5 mmol/kg. They are intended for enteral and parenteral administration. The complex compounds according to the invention are used 1. For NMR diagnosis and diagnostic radiology in the form of their complexes with the ions of the elements with atomic numbers 21–29, 39, 42, 44 and 57–83;
2. For radiodiagnosis and radiotherapy in the form of their complexes with the radioisotopes of the elements with atomic numbers 27, 29, 31, 32, 37–39, 43, 49, 62, 64, 70, 75 and 77.

The agents according to the invention meet the varied requirements for suitability as contrast media for nuclear spin tomography. Thus, after oral or parenteral administration, they are extremely well suited to improve the image obtained with the aid of the nuclear spin tomograph in its informational value. They also show the high effectiveness that is necessary to load the body with the fewest possible quantities of foreign substances, and the good compatibility that is necessary to maintain the noninvasive nature of the studies.

The good water-solubility and low osmolality of the agents according to the invention make it possible to produce highly concentrated solutions to keep the volume burden of the circuit within reasonable limits and to offset the dilution by bodily fluids. In addition, the agents according to the invention show not only high stability in vitro, but also surprisingly high stability in vivo, so that a release or an exchange of the ions—toxic in themselves—and not covalently bonded in the complexes—is carried out only extremely slowly within the time in which the new contrast media are again completely eliminated.

In general, the agents according to the invention are dosed for use as NMR diagnostic agents in quantities of 0.0001–5 mmol/kg, preferably 0.005–0.5 mmol/kg. Details of use are discussed in, for example, H.-J. Weinmann et al., Am. J. of Roentgenology 142, 619 (1984).

Especially low dosages (below 1 mg/kg of body weight) of organ-specific NMR diagnostic agents can be used, for example, to detect tumors and myocardial infarction.

The complex compounds according to the invention can also be used advantageously as susceptibility reagents and as shift reagents for in vivo NMR spectroscopy.

Because of their advantageous radioactive properties and the good stability of the complex compounds that are contained in them, the agents according to the invention are also suitable as radiodiagnostic agents. Details of their use and dosage are described in, e.g., "Radiotracers for Medical Applications," CRC Press, Boca Raton, Fla.

Another imaging method with radioisotopes is the positron-emission tomography, which uses positron-emitting isotopes such as, e.g., $^{43}$Sc, $^{44}$Sc, $^{52}$Fe, $^{55}$Co and $^{68}$Ga (Heiss, W. D.; Phelps, M. E.; Positron Emission Tomography of Brain, Springer Verlag Berlin, Heidelberg, N.Y. 1983).

The compounds according to the invention are also suitable, surprisingly enough, for differentiating malignant and benign tumors in areas without blood-brain barriers.

They are also distinguished in that they are eliminated completely from the body and are thus well-tolerated.

Since the substances according to the invention accumulate in malignant tumors (no diffusion in healthy tissue, but high permeability of tumor vessels), they can also support treating malignant tumors by radiation. These are distinguished from the corresponding diagnosis only by the amount and type of the isotope used. In this case, the goal is the destruction of tumor cells by high-energy shortwave radiation with as small a range of action as possible. For this purpose, interactions of the metals that are contained in the complexes (such as, e.g., iron or gadolinium) with ionizing radiations (e.g., x-rays) or with neutron rays are used. The local radiation dose at the site where the metal complex is located (e.g., in tumors) is significantly enhanced by this effect. To produce the same radiation dose in malignant tissue, the radiation exposure for healthy tissue can be considerably reduced and thus burdensome side effects for the patients can be avoided when such metal complexes are used. The compounds according to the invention are therefore also suitable as radiosensitizing substances in treating malignant tumors by radiation (e.g., use of Mossbauer effects or with neutron capture therapy). Suitable β-emitting ions are, for example, $^{46}$Sc, $^{47}$Sc, $^{48}$Sc, $^{72}$Ga, $^{73}$Ga and $^{90}$Y. Suitable α-emitting ions that have short half-lives are, for example, $^{211}$Bi, $^{212}$Bi, $^{213}$Bi and $^{214}$Bi, whereby $^{212}$Bi is preferred. A suitable photon- and electron-emitting ion is $^{158}$Gd, which can be obtained from $^{157}$Gd by neutron capture.

If the agent according to the invention is intended for use in the variant of radiation therapy that is proposed by R. L. Mills et al. (Nature Vol. 336, (1988), p. 787], the central ion must be derived from a Mossbauer isotope, such as, for example $^{57}$Fe or $^{151}$Eu.

In the in-vivo administration of the therapeutic agents according to the invention, the latter can be administered together with a suitable vehicle such as, for example, serum or physiological common salt solution and together with another protein, such as, for example, human serum albumin. In this case, the dosage depends on the type of cellular disruption, the metal ion used and the type of imaging method.

The therapeutic agents according to the invention are administered parenterally, preferably i.v.

Details of use of radiotherapeutic agents are discussed in, e.g., R. W. Kozak et al. TIBTEC, October 1986, 262.

The agents according to the invention are extremely well suited as x-ray contrast media, whereby it is especially to be emphasized that with them, no signs of the anaphylaxis-like reactions that are known from the iodine-containing contrast media can be detected in biochemical-pharmacological studies. They are especially valuable owing to their advantageous absorption properties in ranges of higher tube voltages for digital subtraction techniques.

In general, the agents according to the invention are dosed for use as x-ray contrast media analogously to, for example, meglumine-diatrizoate in quantities of 0.1–5 mmol/kg, preferably 0.25–1 mmol/kg.

Details of use of x-ray contrast media are discussed in, for example, Barke, Röntgenkontrastmittel [X-Ray Contrast Media], G. Thieme, Leipzig (1970) and P. Thurn, E. B üicheler "Einführung in die Röntgendiagnostik [Introduction into Diagnostic Radiology]," G. Thieme, Stuttgart, N.Y. (1977).

In summary, it has been possible to synthesize new compounds that open up new possibilities in diagnostic and therapeutic medicine.

The examples below are used for a more detailed explanation of the subject of the invention:

Here, the following abbreviations are used:

a) DTPA-monoanhydride-ethyl ester:

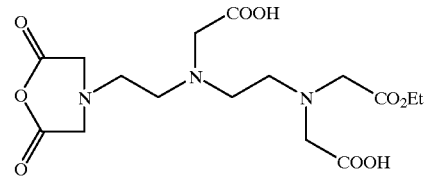

b) sym-DTPA-tetra-t-butyl ester:

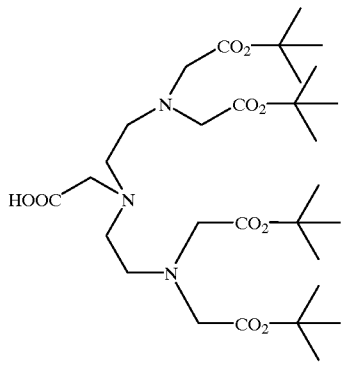

EXAMPLE 1 a) 2H,2H,4H,4H,5H,5H-3-Oxa-perfluoro-tridecanoic acid-t-butyl ester 10.51 g (53.9 mmol) of bromoacetic acid-tert-butyl ester is added in drops to a mixture of 10 g (21.55 mmol) of 1H,1H,2H,2H-perfluorodecan-1-ol and 0.73 g (2.15 mmol) of tetrabutylammonium hydrogen sulfate in 100 ml of 60% potassium hydroxide solution/50 ml of tolue ne while being stirred vigorously at 0° C. It is stirred for 1 hour at 0° C. 200 ml of toluene is added, the aqueous phase is separated and extrated twice with 50 ml of toluene each. The combined organic phases are dried on magnesium sulfate and concentrated by evaporation in a vacuum. The residue is chromatographed on silica gel (mobile solvent: hexane/dichloromethane/acetone=20:10:1).

Yield: 9.72 g (78% of theory) of a colorless, viscous oil

Elementary analysis:

Cld: C, 33.23; H, 2.61; F, 55.85;
Fnd: C, 33.09; H, 2.78; F, 55.71;

b) 2H,2H,4H,4H,5H,5H-3-Oxa-perfluoro-tridecanoic acid 9.0 g (15.56 mmol) of the title compound of Example 1a) is dissolved in 180 ml of trifluoroacetic acid and stirred overnight at room temperature. It is evaporated to the dry state in a vacuum. The residue is recrystallized from methanol/ether.

Yield: 7.80 g (96% of theory) of a colorless solid

Elementary analysis:
Cld: C, 27.60; H, 1.35; F, 61.85;
Fnd: C, 27.48; H, 1.49; F, 61.66;

c) 1,4,7-Tris[N-(2-benzyloxycarbonylamino)-acetyl]-1,4,7,10-tetraazacyclododecane 53.33 g (174 mmol) of N-(benzyloxycarbonyl)-glycine-N-hydroxysuccinimide ester and 17.60 g (174 mmol) of triethylamine are added to 10 g (58 mmol) of 1,4,7,10-tetraazacyclododecane (=cyclene) in 400 ml of toluene and refluxed for 12 hours. It is evaporated to the dry state in a vacuum, the residue is taken up in 400 ml of dichloromethane, and the organic phase is washed twice with 5% aqueous sodium carbonate solution. The organic phase is dried on magnesium sulfate and evaporated to the dry state in a vacuum. The residue is chromatographed on silica gel (mobile solvent: ethyl acetate/ethanol=20:1).

Elementary analysis:
Cld: C, 61.20; H, 6.35; N, 13.15;
Fnd: C, 61.03; H, 6.48; N, 13.02;

d) 1,4,7-Tris[N-(2-benzyloxycarbonylamino)-acetyl-]-10-(N-2H,2H,4H,4H,5H,5H-3-oxa-perfluoro-tridecanoyl)-1,4,7,10-tetraazacyclododecane 20 g (26.82 mmol) of the title compound of Example 1c) and 28.0 g (53.63 mmol) of the title compound of Example 1b) are dissolved in 200 ml of dimethylformamide, and 13.26 g (53.63 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: dichloromethane/acetone=15:1).

Yield: 28.16 g (84% of theory) of a colorless, viscous oil;
Elementary analysis:
Cld: C, 48.05; H, 4.19; N, 7.84; F, 25.84;
Fnd: C, 47.91; H, 4.38; N, 7.71; F, 25.67;

e) 1,4,7-Tris-[N-(2-amino)-acetyl]-10-(N-2H,2H,4H,4H,5H,5H-3-oxa-perfluoro-tridecanoyl)-1,4,7,10-tetraazacyclododecane, trihydrobromide 20 g (16 mmol) of the title compound of Example 1d) is dissolved in 100 ml of acetic acid and added in drops to a solution of 200 ml of hydrogen bromide in glacial acetic acid (33%) whose temperature is 60° C. It is stirred for 1 hour at 60° C. It is cooled to 0° C., and 1,500 ml of diethyl ether is slowly added in drops while being stirred. The deposited precipitate is filtered, rewashed twice with 200 ml of ether and dried in a vacuum furnace (6° C.).

Yield: 16.57 g (95% of theory) of a cream-colored, crystalline solid;
Elementary analysis:
Cld: C, 28.64; H, 3.42; N, 8.99; F, 29.62; Br, 21.99;
Fnd: C, 28.51; H, 3.60; N, 8.72; F, 29.41; Br, 21.65;

f) Gd Complex of 1,4,7-tris(N-carboxylatomethyl)-10-(N-1-methyl-2-oxo-3-aza-4-carboxy-butyl)-1,4,7,10-tetraazacyclododecane 77 g (103.1 mmol) of 10-[4-carboxy-1-methyl-2-oxo-3-azabutyl]-1,4,7-tris(tert-butoxycarbonyl)-1,4,7,10-tetraazacyclododecane is dissolved in 500 ml of trifluoroacetic acid and stirred for 3 hours at room temperature. It is evaporated to the dry state, the residue is taken up in 300 ml of water, and the solution is added to a column, filled with Reillex® 425 PVP. It is eluted with water. The product-containing fractions are combined and evaporated to the dry state, and the residue is recrystallized from methanol/acetone.

Yield: 44.04 g (84% of theory) of a colorless, hygroscopic solid; Water content: 6.5%;
Elementary analysis (relative to anhydrous substance):
Cld: C, 47.99; H, 6.99; N, 14.73;
Fnd: C, 47.83; H, 7.12; N, 14.55;

15.27 g (42.06 mmol) of gadolinium oxide is added to 40 g (84.12 mmol) of the above-obtained tetra acid, dissolved in 400 ml of water, and it is heated for 3 hours to 90° C. It is evaporated to the dry state (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 50.53 g (93% of theory) of a colorless, crystalline powder
Water content: 2.5%
Elementary analysis (relative to anhydrous substance):
Cld: C, 36.24; H, 4.80; N, 11.12; Gd, 24.97;
Fnd: C, 36.35; H, 4.95; N, 10.98; Gd, 24.80;

g) 1,4,7-Tris{,1,4,7-tris(N-carboxylatomethyl)-10-(N-1-methyl-3,6-diaza-2,5,8-trioxo-octane-1,8-diyl)-1,4,7,10-tetraazacyclododecane, Gd complex}-10-(N-2H,2H,4H,4H,5H,5H-3-oxa-perfluoro-tridecanoyl)-1,4,7,10-tetraazacyclododecane 15.74 g (25 mmol) of the Gd complex, described in Example 1f), of 10-(4-carboxy-1-methyl-2-oxo-3-azabutyl)-1,4,7,10-tetraazacyclododecane-1,4,7-triacetic acid, 2.57 g of sodium bromide (25 mmol) and 5.75 g (50 mmol) of N-hydroxysuccinimide are dissolved in 200 ml of dimethyl sulfoxide at 50° C. After cooling to room temperature, 10.32 g (50 mmol) of N,N'-dicyclohexylcarbodiimide is added and preactivated for 60 minutes. A solution of 3 g (2.75 mmol) of the title compound that is described in Example 1e) and 5.06 g (50 mmol) of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-1 ultrafiltration membrane (cut-off/1,000 Da), and low-molecular components are removed. The retentate is then freeze-dried.

Yield: 6.42 g (87% of theory)
$H_2O$ content: 10.1%
Elementary analysis (relative to anhydrous substance):
Cld: C, 37.13; H, 4.51; N, 11.48; F, 12.03; Gd, 17.57;
Fnd: C, 37.01; H, 4.71; N, 11.23; F, 11.84; Gd, 17.38;

EXAMPLE 2

1,4,7-Tris{1,4,7-tris(N-carboxylatomethyl)-10-(N-1-methyl-3,6-diaza-2,5,8-trioxo-octane-1,8-diyl)-1,4,7,10-tetraazacyclododecane, Dy complex}-10-(N-2H,2H,4H,4H,5H,5H-3-oxa-perfluoro-tridecaonyl)-1,4,7,10-tetraazacyclododecane 10 g (3.72 mmol) of the title compound of Example 1g) is dissolved in 200 ml of water, and 1.52 g (16.86 mmol) of oxalic acid is added. It is stirred for 8 hours at 60° C. It is cooled to 0° C., and precipitated gadolinium-oxalate is filtered out. 2.08 g (5.58 mmol) of dysprosium oxide is added to the filtrate and heated for 5 hours to 90° C. The solution is evaporated to the dry state, and the residue is chromatographed on RP-18 (mobile solvent: gradient consisting of acetonitrile/water).

Yield: 8.74 g (87% of theory) of a vitreous solid
Water content: 9.3%
Elementary analysis (relative to anhydrous substance):
Cld: C, 36.92; H, 4.48; N, 11.41; F, 11.96; Dy, 18.05;
Fnd: C, 36.81; H, 4.62; N, 11.35; F, 11.81; Dy, 17.84;

EXAMPLE 3

1,4,7-Tris{1,4,7-tris(N-carboxylatomethyl)-10-(N-1-methyl-3,6-diaza-2,5,8-trioxo-octane-1,8-diyl)-1,4,7,10-tetraazacyclododecane, Fe complex}-10-(N-2H,2H,4H,4H,5H,5H-3-oxa-perfluorotridecanoyl)-1,4,7,10-tetraazacyclododecane 10 g (3.72 mmol) of the title compound of Example 1g) is dissolved in 200 ml of water, and 1.52 mg (16.86 mmol) of oxalic acid is added. It is stirred for 8 hours at 80° C. It is cooled to 0° C., and precipitated gadolinium-oxalate is filtered out. 3.93 g (11.16 mmol) of iron(III)-acetylacetonate is added to the filtrate, and it is heated for 5 hours to 90° C. The solution is evaporated to the dry state, and the residue is chromatographed on RP-18 (mobile solvent: gradient consisting of acetonitrile/water).

Yield: 7.17 g (81% of theory) of a vitreous solid
Water content: 7.5%
Elementary analysis (relative to anhydrous substance):
Cld: C, 41.88; H, 5.08; N, 12.94; F, 13.57; Fe, 7.08;
Fnd: C, 41.65; H, 5.21; N, 12.75; F, 13.41; Fe, 6.93;

EXAMPLE 4 a) 1,4,7-Tris-(N-benzyloxycarbonyl)-10-(N-2H,2H,4H,4H,5H,5H-3-oxa-perfluorotridecanoyl)-1,4,7,10-tetraazacyclododecane 30 g (52.20 mmol) of 1,4,7-tris-(benzyloxycarbonyl)-1,4,7,10-tetraazacyclododecane (≅ tri-Z-cyclene) and 54.51 g (104.4 mmol) are dissolved in 300 ml of dimethylformamide, and 25.82 g (104.4 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: dichloromethane/2-propanol=20:1).

Yield: 44.5 (79% of theory) of a colorless, viscous oil
Elementary analysis:
Cld: C, 48.99; H, 4.02; N, 5.19; F, 29.94;
Fnd: C, 48.75; H, 4.21; N, 5.03; F, 29.75;

b) 1-(N-H,2H,4H,4H,5H,5H-3-Oxa-perfluorotridecanoyl)-1,4,7,10-tetraazacyclododecane 30 g (27.81 mmol) of the title compound of Example 4a) is dissolved in 500 ml of methanol, and 5 g of palladium catalyst (10% Pd/C) is added. It is hydrogenated overnight at room temperature. Catalyst is filtered out, and the filtrate is evaporated to the dry state in a vacuum.

Yield: 18.81 g (quantitative) of a vitreous, colorless solid
Elementary analysis:
Cld: C, 35.51; H, 3.73; N, 8.28; F, 47.75;
Fnd: C, 35.40; H, 3.91; N, 8.14; F, 47.53;

c) 1,4,7-Tris[1,4,7-tris(N-carboxylatomethyl)-10-(N-1-methyl-3-aza-2,5-dioxo-pentane-1,5-diyl)-1,4,7,10-tetraazacyclododecane, Gd complex]-10-(2H,2H,4H,4H,5H,5H-3-oxa-perfluoro-tridecanoyl)-1,4,7,10-tetraazacyclododecane 16.75 g (25.61 mmol) of the Gd complex, described in Example 1f), of 10-(4-carboxy-1-methyl-2-oxo-3-azabutyl)-1,4,7,10-tetraazacyclododecane-1,4,7-triacetic acid and 2.78 sodium bromide (27 mmol) are dissolved in 200 ml of dimethyl sulfoxide at 50° C. After cooling to room temperature, 12.37 g (50 mmol) of 2-ethoxy-1-ethoxycarbonyl-1,2-dihydroquinoline and 3 g (2.75 mmol) of the title compound described in Example 4b) are added, and it is stirred overnight at room temperature. The suspension that is obtained is then mixed with sufficient acetone until complete precipitation occurs, the precipitate is suctioned off, dried, taken up in water and desalinated with an AMICON® YM-1 ultrafiltration membrane (cut-off/1,000 Da), and low-molecular components are removed. The retentate is then freeze-dried.

Yield: 9.70 g (87% of theory);
H₂O content: 8.9%
Elementary analysis (relative to anhydrous substance):
Cld: C, 36.82; H, 4.37; N, 10.60; Gd, 18.78; F, 12.86;
Fnd: C, 36.70; H, 4.18; N, 10.45; Gd, 18.61; F, 12.71;

EXAMPLE 5 a) 2H,2H,4H,4H,5H,5H-3-Oxa-perfluoro-pentadecanoic acid-t-butyl ester 10.51 g (53.9 mmol) of bromoacetic acid-tert-butyl ester is added in drops to a mixture of 12.16 g (21.55 mmol) of 1H,1H,2H,2H-perfluorododecan-1-ol and 0.73 g (2.15 mmol) of tetrabutylammonium hydrogen sulfate in 100 ml of 60% potassium hydroxide solution/50 ml of toluene while being stirred vigorously at 0° C. It is stirred for 1 hour at 0° C. 200 ml of toluene is added, the aqueous phase is separated and extracted twice with 50 ml of toluene each. The combined organic phases are dried on magnesium sulfate and concentrated by evaporation in a vacuum. The residue is chromatographed on silica gel (mobile solvent: hexane/dichloromethane/acetone=20:10:1).

Yield: 11.42 g (81% of theory) of a colorless, viscous oil
Elementary analysis:
Cld: C, 29.37; H, 2.31; F, 60.98;
Fnd: C, 29.28; H, 2.42; F, 60.81;

b) 2H,2H,4H,4H,5H,5H-3-Oxa-perfluoropentadecanoic acid 9.0 g (15.56 mmol) of the title compound of Example 5a) is dissolved in 180 ml of trifluoroacetic acid, and it is stirred overnight at room temperature. It is evaporated to the dry state in a vacuum. The residue is recrystallized from methanol/ether.

Yield: 9.29 g (96% of theory) of a colorless solid
Elementary analysis:
Cld: C, 27.03; H, 1.13; F, 64.12;
Fnd: C, 26.91; H, 1.24; F, 64.01;

c) 1,4,7-Tris[N-(2-benzyloxycarbonylamino)-acetyl-]-10-(N-2H,2H,4H,4H,5H,5H-3-oxa-perfluoropentadecanoyl)-1,4,7,10-tetraazacyclododecane 20 g (26.82 mmol) of the title compound of Example 1c) and 33.35 g (53.6 mmol) of the title compound of Example 5b) are dissolved in 200 ml of dimethylformamide, and 13.26 g (53.6 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: dichloromethane/acetone=15:1).

Yield: 29.33 (81% of theory) of a colorless, viscous oil
Elementary analysis:
Cld: C, 46.26; H, 3.88; N, 7.26; F, 29.55;
Fnd: C, 46.13; H, 3.68; N, 7.31; F, 29.44;

d) 1,4,7-Tris-[N-(2-amino)-acetyl]-10-(N-2H,2H,4H,4H,5H,5H-3-oxa-perfluoro-pentadecanoyl)-1,4,7,10-tetraazacyclododecane, trihydrobromide 15 g (11.11 mmol) of the title compound of Example 5c) is dissolved in 100 ml of acetic acid and added in drops to a solution of 150 ml of hydrogen bromide in glacial acetic acid (33%) whose temperature is 60° C. It is stirred for 1 hour at 60° C. It is cooled to 0° C., and 1,500 ml of diethyl ether is slowly added in drops while being stirred. The deposited precipitate is filtered off, rewashed twice with 200 ml of ether and dried in a vacuum furnace (60° C.).

Yield: 12.7 g (96% of theory) of a cream-colored, crystalline solid

Elementary analysis:
Cld: C, 28.25; H, 3.13; N, 8.24; F, 33.52; Br, 20.14;
Fnd: C, 28.14; H, 3.24; N, 8.13; F, 33.38; Br, 20.01;

e) 1,4,7-Tris{1,4,7-tris(N-carboxylatomethyl)-10-(N-1-methyl-3,6-diaza-2,5,8-trioxo-octane-1,8-diyl)-1,4,7,10-tetraazacyclododecane, Gd complex}-10-(N-2H,2H,4H,4H,5H,5H-3-oxa-perfluoro-pentadecanoyl)-1,4,7,10-tetraazacyclododecane 15.74 g (25 mmol) of the Gd complex, described in Example 1f), of 10-(4-carboxy-1-methyl-2-oxo-3-azabutyl)-1,4,7,10-tetraazacyclododecane-1,4,7-triacetic acid, 2.57 g of sodium bromide (25 mmol) and 5.75 g (50 mmol) of N-hydroxysuccinimide are dissolved in 200 ml of dimethyl sulfoxide at 50° C. After cooling to room temperature, 10.32 g (50 mmol) of N,N'-dicyclohexylcarbodiimide is added and preactivated for 60 minutes. A solution of 3.27 g (2.75 mmol) of the title compound that is described in Example 5d) and 5.06 g (50 mmol) of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered off, and the filtrate is desalinated with an AMICON® YM-1 ultrafiltration membrane (cut-off/1,000 Da), and low-molecular components are removed. The retentate is then freeze-dried.

Yield: 6.74 g (88% of theory)
$H_2O$ content: 6.8%
Elementary analysis (relative to anhydrous substance):
Cld: C, 36.66; H, 4.34; N, 11.07; F, 14.33; Gd, 16.94;
Fnd: C, 36.49; H, 4.42; N, 11.01; F, 14.21; Gd, 16.81;

EXAMPLE 6 a) 1,4,7-Tris(N-3,6,9-carboxymethyl-12-aza-11-oxo-3,6,9,12-tetraaza-tetradecane-1,14-dicarboxylic acid-monoamide)-10-(N-2H,2H,4H,4H,5H,5H-3-oxa-perfluoro-tridecanoyl)-1,4,7,10-tetraazacyclododecane 10.43 g (27.5 mmol) of DTPA-monoanhydride-ethyl ester and 1 g (8.19 mmol) of 4-(dimethylamino)-pyridine are added to 5 g (4.59 mmol) of the title compound of Example 1e) and 50 g of pyridine in 50 ml of dimethylformamide. It is stirred for 24 hours at 50° C. It is evaporated to the dry state in a vacuum, the residue is taken up in 200 ml of water, and it is brought to pH 13 with 2N sodium hydroxide solution. It is stirred for 6 hours at room temperature. It is set at pH 2 with 10% aqueous hydrochloric acid, and the solution is dialyzed with an AMICON® YM-1 ultrafiltration membrane (cut-off 1,000 Da) to remove from it low-molecular components. The retentate is then freeze-dried.

Yield: 8.24 g (91% of theory)
$H_2O$ content: 7.5%
Elementary analysis (relative to anhydrous substance):
Cld: C, 41.38; H, 4.95; N, 11.36; F, 16.36;
Fnd: C, 41.28; H, 5.07; N, 11.29; F, 16.27;

b) 1,4,7-Tris(N-3,6,9-carboxymethyl-12-aza-11-oxo-3,6,9,12-tetraaza-tetradecane-1,14-dicarboxylic acid-14-monoamide, Gd complex, monosodium salt)-10-(N-2H,2H,4H,4H,5H,5H,3-oxa-perfluoro-tridecanoyl)-1,4,7,10-tetraazacyclododecane 2.54 g (7.59 mmol) of gadolinium acetate is added to 5 g (2.53 mmol) of the title compound of Example 6b), dissolved in 200 ml of water. Then, it is stirred for 1 hour at 60° C. It is allowed to cool to room temperature, set at pH 7.2 with 2N aqueous sodium hydroxide solution, and the solution is dialyzed in an ultrafiltration cell AMICON® YM-1 (cut-off 1,000 Da, 6 passes). The contents of the ultrafiltration cell are freeze-dried.

Yield: 6.08 g (96% of theory)
Water content: 9.1%
Elementary analysis (relative to anhydrous substance):
Cld: C, 32.64; H, 3.42; N, 8.96; F, 12.91; Gd, 18.85; Na, 2.76;
Fnd: C, 32.47; H, 3.57; N, 8.90; F, 12.84; Gd, 18.67; Na, 2.55;

EXAMPLE 7 a) 1,4,7-Tris{(N-3,6,9-carboxymethyl-12-aza-11-oxo-3,6,9,12-tetraaza-tetradecane-1,14-dicarboxylic acid-14-monoamide)}-10-(N-2H,2H,4H,4H,5H,5H-3-oxa-perfluoro-pentadecanoyl)-1,4,7,10-tetraazacyclododecane 10.43 g (27.5 mmol) of DTPA-monoanhydride-ethyl ester and 1 g (8.19 mmol) of 4-(dimethylamino)-pyridine are added to 5.46 g (4.59 mmol) of the title compound of Example 5d) and 50 g of pyridine in 50 ml of dimethylformamide. It is stirred for 24 hours at 50° C. It is evaporated to the dry state in a vacuum, the residue is taken up in 200 ml of water and brought to pH 13 with 2N sodium hydroxide solution. It is stirred for 6 hours at room temperature. It is set at pH 2 with 10% aqueous hydrochloric acid, and the solution is dialyzed with an AMICON® YM-1 ultrafiltration membrane (cut-off 1,000 Da) to remove from it low-molecular components. The retentate is then freeze-dried.

Yield: 8.85 g (93% of theory)
$H_2O$ content: 6.3%
Elementary analysis (relative to anhydrous substance):
Cld: C, 40.55; H, 4.71; N, 10.81; F, 19.24;
Fnd: C, 40.41; H, 4.85; N, 10.74; F, 19.11;

b) 1,4,7-Tris[(N-3,6,9-carboxymethyl-12-aza-11-oxo-3,6,9,12-tetraaza-tetradecane-1,14-dicarboxylic acid-14-monoamide), Gd complex, monosodium salt]-10-(N-2H,2H,4H,4H,5H,5H-3-oxa-perfluoro-pentadecanoyl)-1,4,7,10-tetraazacyclododecane 2.54 g (7.59 mmol) of gadolinium acetate is added to 5.25 g (2.53 mmol) of the title compound of Example 7a), dissolved in 200 ml of water. Then, it is stirred for 1 hour at 60° C. It is allowed to cool to room temperature, set at pH 7.2 with 2N aqueous sodium hydroxide solution, and the solution is dialyzed in an ultrafiltration cell AMICON® YM-1 (cut-off 1,000 Da, 6 passes). The contents of the ultrafiltration cell are freeze-dried.

Yield: 6.42 g (97% of theory)
Water content: 10.1%
Elementary analysis (relative to anhydrous substance):
Cld: C, 32.16; H, 3.74; N, 8.57; F, 15.26; Gd, 18.04; Na, 2.64;
Fnd: C, 32.01; H, 3.93; N, 8.61; F, 15.10; Gd, 17.91; Na, 2.43;

EXAMPLE 8 a) 1,4,7-Tris{3,9-bis(N-t-butyloxycarbonylmethyl)-6-[N-3-aza-2,5-dioxo-pentane-1,5-diyl]-3,6,9-triazaundecanedioic acid-di-t-butyl ester}-10-(N-2H,2H,4H,4H,5H,5H-3-oxa-perfluoro-tridecanoyl)-1,4,7,10-tetraazacyclododecane 6.34 g (55.1 mmol) of N-hydroxysuccinimide and 11.37 g (55.1 mmol) of N,N'-dicyclohexylcarbodiimide are added to 17 g (27.54 mmol) of sym-DTPA-tetra-tert-butyl ester, dissolved in 300 ml of dimethylformamide, at 0° C., and it is stirred for one hour at this temperature. Then, it is stirred for 3 hours at room temperature. 5 g (4.59 mmol) of the title compound of Example 1e) and 11.13 g (110 mmol) of triethylamine are added to this solution. It is stirred for 24 hours at room temperature. The solution is evaporated to the dry state, and the residue is taken up in 500 ml of dichloromethane. Dicyclohexylurea is filtered out, and the filtrate is washed twice with 250 ml of 5% aqueous sodium carbonate solution. The organic phase is dried on magnesium sulfate and evaporated to the dry state in a vacuum. The residue is chromatographed on silica gel (mobile solvent: dichloromethane/methanol=20:1).

Yield: 9.84 g (81% of theory) of a colorless, viscous oil
Elementary analysis:
Cld: C, 52.64; H, 7.35; N, 8.47; F, 12.20;
Fnd: C, 52.51; H, 7.45; N, 8.38; F, 12.07;

b) 1,4,7-Tris{N-3,3,6-tris(carboxylatomethyl)-6-[N-3-aza-2,5-dioxo-pentane-1,5-diyl]-3,6,9-triazaundecane-1,11-dioic acid, Gd complex, monosodium salt}-10-2H,2H,4H,4H,5H,5H-3-oxa-perfluoro-tridecanoyl)-1,4,7,10-tetraazacyclododecane 9 g (3.4 mmol) of the title compound of Example 8a) is dissolved in 200 ml of trifluoroacetic acid and stirred for 12 hours at room temperature. It is evaporated to the dry state in a vacuum. The residue is dissolved in 200 ml of water and set at pH 4 with 10% aqueous sodium hydroxide solution. Then, 1.85 g (5.1 mmol) of gadolinium oxide is added, and it is stirred for 2 hours at 70° C. It is cooled to room temperature, and set at pH 7.2 with 10% sodium hydroxide solution. The solution is mixed with 3 g of activated carbon, stirred for one hour at room temperature and filtered. The filtrate is filled in an ultrafiltration cell and dialyzed (AMICON® YM-1 (cut-off 1,000 Da)). Dialysis is performed until the eluate has reached a conductivity of 10 µS. Then, the contents of the ultrafiltration cell are freeze-dried.

Yield: 7.91 g (93% of theory) of a colorless, amorphous powder
Water content: 7.9%
Elementary analysis (relative to anhydrous substance):
Cld: C, 32.64; H, 3.42; N, 8.96; F, 12.91; Gd, 18.85; Na, 2.76;
Fnd: C, 32.48; H, 3.55; N, 8.87; F, 12.80; Gd, 18.79; Na, 2.48;

EXAMPLE 9 a) 1,4,7-Tris{N-3,9-bis(N-t-butyloxycarbonylmethyl)-6-[N-3-aza-2,5-dioxo-pentane-1,5-diyl]-3,6,9-triazaundecane-1,11-dioic acid-di-t-butyl ester}-10-(N-2H,2H,4H,4H,5H,5H-3-oxa-perfluoro-tridecanoyl)-1,4,7,10-tetraazacyclododecane 5.8 g (50.4 mmol) of N-hydroxysuccinimide and 10.4 g (50.4 mmol) of N,N'-dicyclohexylcarbodiimide are added to 15.54 g (25.20 mmol) of sym-DTPA-tetra-tert-butyl ester, dissolved in 200 ml of dimethylformamide, at 0° C., and it is stirred for one hour at this temperature. Then, it is stirred for 3 hours at room temperature. 5 g (4.2 mmol) of the title compound of Example 5d) and 11.13 g (100 mmol) of triethylamine are added to this solution. It is stirred for 24 hours at room temperature. The solution is evaporated to the dry state, and the residue is taken up in 300 ml of dichloromethane. Dicyclohexylurea is filtered out, and the filtrate is washed twice with 150 ml of 5% aqueous sodium carbonate solution. The organic phase is dried on magnesium sulfate and evaporated to the dry state in a vacuum. The residue is chromatographed on silica gel (mobile solvent: dichloromethane/methanol=20:1).

Yield: 9.76 g (87% of theory) of a colorless, viscous oil
Elementary analysis:
Cld: C, 53.06; H, 7.28; N, 8.39; F, 12.09;
Fnd: C, 52.90; H, 7.41; N, 8.27; F, 12.93;

b) 1,4,7-Tris{N-3,9-bis(N-carboxylatomethyl)-6-[N-3-aza-2,5-dioxo-pentane-1,5-diyl]-3,6,9-triazaundecane-1-carboxylato-11-acid, Gd complex, sodium salt}-10-(N-2H,2H,4H,4H,5H,5H-3-oxa-perfluoro-pentadecanoyl)-1,4,7,10-tetraazacyclododecane 9 g (3.37 mmol) of the title compound of Example 9a) is dissolved in 200 ml of trifluoroacetic acid and stirred for 12 hours at room temperature. It is evaporated to the dry state in a vacuum. The residue is dissolved in 200 ml of water and set at pH 4 with 10% aqueous sodium hydroxide solution. Then, 1.83 g (5.06 mmol) of gadolinium oxide is added, and it is stirred for 2 hours at 70° C. It is cooled to room temperature and set at pH 7.2 with 10% aqueous sodium hydroxide solution. The solution is mixed with 3 g of activated carbon, stirred for 1 hour at room temperature and filtered. The filtrate is filled in an ultrafiltration cell and dialyzed (AMICON® YM-1 (cut-off 1,000 Da)). Dialysis is performed until the eluate has reached a conductivity of 10 µS. Then, the contents of the ultrafiltration cell are freeze-dried.

Yield: 8.24 g (94% of theory) of a colorless, amorphous powder
Water content: 10.1%
Elementary analysis (relative to anhydrous substance):
Cld: C, 32.31; H, 3.29; N, 8.61; F, 15.33; Gd, 18.13; Na, 2.65;
Fnd: C, 32.21; H, 3.42; N, 8.59; F, 15.24; Gd, 18.03; Na, 2.24;

EXAMPLE 10 a) 1,4,7-Tris{N-3,9-bis(N-t-butyloxycarbonylmethyl)-6-[N-(2-oxo)-methyl]-3,6,9-triazaundecane-1,11-dioic acid-di-t-butyl ester}-10-(N-2H,2H,4H,4H,5H,5H-3-oxa-perfluoro-tridecanoyl)-1,4,7,10-tetraazacyclododecane 10.21 g (88.7 mmol) of N-hydroxysuccinimide and 18.30 g (88.7 mmol) of N,N'-dicyclohexylcarbodiimide are added to 27.35 g (44.35 mmol) of sym-DTPA-tetra-tert-butyl ester, dissolved in 400 ml of dimethylformamide at 0° C., and it is stirred for one hour at this temperature. Then, it is stirred for 3 hours at room temperature. 5 g (7.39 mmol) of the title compound of Example 4b) and 17.91 g (177 mmol) of triethylamine are added to this solution. It is stirred for 24 hours at room temperature. The solution is evaporated to the dry state, and the residue is taken up in 400 ml of dichloromethane. Dicyclohexylurea is filtered out, and the filtrate is washed twice with 200 ml of 5% aqueous sodium carbonate solution. The organic phase is dried on magnesium sulfate and evaporated to the dry state in a vacuum. The residue is chromatographed on silica gel (mobile solvent: dichloromethane/methanol=20:1).

Yield: 16.65 g (91% of theory) of a colorless, viscous oil
Elementary analysis:
Cld: C, 53.37; H, 7.49; N, 7.35; F, 13.05;
Fnd: C, 53.28; H, 7.61; N, 7.27; F, 12.96;

b) 1,4,7-Tris{N-3,3,9-tris(carboxylatomethyl)-6-(N-(2-oxo)-methyl]-3,6,9-triazaundecane-1-carboxylato-11-acid, Gd complex, sodium salt}-10-(N-2H,2H,4H,4H,5H,5H,3-oxa-perfluoro-tridecanoyl)-1,4,7,10-tetraazacyclododecane 9 g (3.64 mmol) of the title compound of Example 10a) is dissolved in 200 ml of trifluoroacetic acid, and it is stirred for 12 hours at room temperature. It is evaporated to the dry state in a vacuum. The residue is dissolved in 200 ml of water and set at pH 4 with 10% aqueous sodium hydroxide solution. Then, 1.98 g (5.46 mmol) of gadolinium oxide is added, and it is stirred for 2 hours at 70° C. It is cooled to room temperature and set at pH 7.2 with 10% aqueous sodium hydroxide solution. The solution is mixed with 3 g of activated carbon, stirred for 1 hour at room temperature and filtered. The filtrate is filled into an ultrafiltration cell and dialyzed (AMICON® YM-1 (cut-off 1,000 Da)). Dialysis is performed until the eluate has reached a conductivity of 10 µS. Then, the contents of the ultrafiltration cell are freeze-dried.

Yield: 8.05 g (95% of theory) of a colorless, amorphous powder

Water content: 6.9%

Elementary analysis (relative to anhydrous substance):
Cld: C, 31.95; H, 3.29; N, 7.81; F, 13.86; Gd, 20.24; Na, 2.96;
Fnd: C, 31.88; H, 3.41; N, 7.72; F, 13.74; Gd, 20.11; Na, 2.73;

EXAMPLE 11 a) 1,4,7-Tris(N-benzyloxycarbonyl)-10-N-(2H,2H,4H,4H, 5H,5H-3-oxa-perfluoro-pentadecanoyl)-1,4,7,10-tetraazacyclododecane 21.65 g (34.8 mmol) of the title compound of Example 5b) and 10 g (17.4 mmol) of 1,4,7-tris-(benzyloxycarbonyl)-1,4,7,10-tetraazacyclododecane are dissolved in 200 ml of dimethylformamide, and 8.61 g (34.8 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: dichloromethane/2-propanol=20:1).

Yield: 17.02 (83% of theory) of a colorless, viscous oil
Elementary analysis:
Cld: C, 46.87; H, 3.68; N, 4.75; F, 33.84;
Fnd: C, 46.63; H, 3.84; N, 4.61; F, 33.72;

b) 1-N-(2H,2H,4H,4H,5H,5H-3-oxa-perfluoro-pentadecanoyl)-1,4,7,10-tetraaza-cyclododecane 20 g (16.97 mmol) of the title compound of Example 11a) is dissolved in 400 ml of methanol, and 3 g of palladium catalyst (10% Pd/C) is added. It is hydrogenated overnight at room temperature. Catalyst is filtered out, and the filtrate is evaporated to the dry state in a vacuum.

Yield: 13.17 g (quantitative) of a vitreous, colorless solid
Elementary analysis:
Cld: C, 34.03; H, 3.25; N, 7.22; F, 51.38;
Fnd: C, 33.91; H, 3.42; N, 7.11; F, 51.24;

c) 1,4,7-Tris{1,4,7-tris[(N-carboxylatomethyl)]-10-[N-methyl-3-aza-2,5-dioxo-pentane-1,5-diyl]-1,4,7,10-tetraazacyclododecane, Gd complex}-10-(N-2H,2H,4H, 4H,5H,5H-3-oxa-perfluoro-pentadecanoyl)-1,4,7,10-tetraazacyclododecane 40.55 g (64.4 mmol) of the Gd complex, described in Example 1f), of 10-(4-carboxy-1-methyl-2-oxo-3-azabutyl)-1,4,7,10-tetraazacyclododecane-1,4,7-triacetic acid and 6.63 g of sodium bromide (64.4 mmol) are dissolved in 500 ml of dimethyl sulfoxide at 50° C. After cooling to room temperature, 10.0 g (12.88 mmol) of the title compound that is described in Example 11b) and 31.9 g (129 mmol) of 2-ethoxy-1-ethoxycarbonyl-1,2-dihydroquinoline are added. It is stirred overnight at room temperature. The suspension that is obtained is then mixed with sufficient acetone until complete precipitation occurs, the precipitate is suctioned off, dried, taken up in water and desalinated with an AMICON® YM-1 ultrafiltration membrane (cut-off/1,000 Da), and low-molecular components are removed. The retentate is then freeze-dried.

Yield: 30.61 g (91% of theory)
H₂O content: 11.4%
Elementary analysis (relative to anhydrous substance):
Cld: C, 36.33; H, 4.21; N, 10.19; F, 15.28; Gd, 18.06;
Fnd: C, 36.18; H, 4.40; N, 10.03; F, 15.17; Gd, 17.91;

EXAMPLE 12 a) N-Ethyl-N-(perfluorooctylsulfonyl)-amino-acetic acid-t-butyl ester 20 g (37.94 mmol) of N-ethylperfluorooctylsulfonamide and 15.73 g (113.8 mmol) of potassium carbonate are suspended in 200 ml of acetone, and 14.80 g (75.87 mmol) of bromoacetic acid-tert-butyl ester is added in drops at 60° C. It is stirred for 3 hours at 60° C. Salts are filtered out, and the filtrate is evaporated to the dry state in a vacuum. The residue is chromatographed on silica gel (mobile solvent: hexane/dichloromethane/acetone=10:10:1). After the product-containing fractions are concentrated by evaporation, the residue is recrystallized from methanol/ether.

Yield: 21.66 g (89% of theory) of a waxy, colorless solid
Elementary analysis:
Cld: C, 29.96; H, 2.51; F, 50.36; N, 2.18; S, 5.00;
Fnd: C, 29.81; H, 2.70; F, 50.15; N, 2.30; S, 4.83;

b) N-Ethyl-N-(perfluorooctylsulfonyl)-amino-acetic acid 20 g (31.18 mmol) of the title compound of Example 12a) is dissolved in 20 ml of trifluoroacetic acid and stirred overnight at room temperature. It is evaporated to the dry state in a vacuum. The residue is recrystallized from methanol/ether.

Yield: 17.34 g (95% of theory) of a colorless, crystalline solid
Elementary analysis:
Cld: C, 24.63; H, 1.38; F, 55.19; N, 2.39; S, 5.48;
Fnd: C, 24.48; H, 1.50; F, 55.01; N, 2.17; S, 5.59;

c) 1,4,7-Tris(N-benzyloxycarbonyl)-10-[2-(N-ethyl-N-perfluorooctylsulfonyl)-amino[acetyl-1,4,7,10-tetraazacyclododecane 17 g (29.04 mmol) of the title compound of Example 12c) and 8.34 g (14.52 mmol) of 1,4,7-tris-(benzyloxycarbonyl)-1,4,7,10-tetraazacyclododecane are dissolved in 200 ml of dimethylformamide, and 7.18 g (29.04 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: dichloromethane/acetone=20:1).

Yield: 13.1 (79% of theory) of a colorless, viscous oil
Elementary analysis:
Cld: C, 46.28; H, 3.88; N, 6.13; F, 28.28; S, 2.81;
Fnd: C, 46.17; H, 3.99; N, 6.04; F, 28.17; S, 2.74;

d) 1-[2-(N-Ethyl-N-perfluoroacetylsulfonyl) -amino]-acetyl-1,4,7, 10-tetraazacyclododecane 12 g (10.5 mmol) of the title compound of Examaple 12c) is dissolved in 200 ml of methanol, and 2 g of palladium catalyst (10% Pd/C) is added. It is hydrogenated overnight at room temperature. Catalyst is filtered out, and the filtrate is evaporated to the dry state in a vacuum.

Yield: 7.77 g (quantitative) of a vitreous, colorless solid
Elementary analysis:
Cld: C, 32.48; H, 3.54; N, 9.47; F, 43.67; S, 4.34;
Fnd: C, 32.36; H, 3.61; N, 9.38; F, 43.58; S, 4.27;

e) 1,4,7-Tris{1,4,7-tris[(N-carboxylatomethyl)]-10-[N-1-methyl-3-aza-2,5-dioxo-pentane-1,5-diyl]-1,4,7,10-tetraazacyclododecane, Gd complex}-10-[2-(N-ethyl-N-perfluorooctylsulfonyl)-amino]-acetyl-1,4,7,10-tetraazacyclododecane 29.8 g (47.33 mmol) of the Gd complex, described in Example 1f, of 10-(4-carboxy-1-methyl-2-oxo-3-azabutyl)-1,4,7,10-tetraazacyclododecane-1,4,7-triacetic acid and 4.87 g of sodium bromide (47.33 mmol) are dissolved in 400 ml of dimethyl sulfoxide at 50° C. After cooling to room temperature, 7 g (9.47 mmol) of the title compound that is described in Example 12d and 12.12 g (49 mmol) of 2-ethoxy-1-ethoxycarbonyl-1,2-dihydroquinoline are added. The suspension that is obtained is then mixed with sufficient acetone until complete precipitation occurs, the precipitate is suctioned off, dried, taken up in water and desalinated with an AMICON® YM-1 ultrafiltration membrane (cut-off/1,000 Da), and low-molecular components are removed. The retentate is then freeze-dried.

Yield: 22.43 g (92% of theory)
$H_2O$ content: 10.6%
Elementary analysis (relative to anhydrous substance):
Cld: C, 35.92; H, 4.31; N, 10.88; F, 12.54; Gd, 18.32; S, 1.25;
Fnd: C, 35.86; H, 4.40; N, 10.82; F, 15.47; Gd, 18.28; S, 1.16;

EXAMPLE 13 a) Gadolinium complex of 10-[4-carboxy-2-oxo-3-azabutyl]-1,4,7,10-tetraazacyclo-dodecane-1,4,7-triacetic acid 25 g (36.45 mmol) of 10-[4-(t-butyloxycarbonyl)-2-oxo-3-azabutyl]-1,4,7,10-tetraazacyclo-dodecane-1,4,7-triacetic acid-tri-tert-butyl ester is dissolved in 300 ml of trifluoroacetic acid and stirred for 3 hours at room temperature. It is evaporated to the dry state, the residue is taken up in 300 ml of water, and the solution is added to a column, filled with Reillex® 425 PVP. It is eluted with water. The product-containing fractions are combined and evaporated to the dry state, the residue is recrystallized from methanol/acetone.

Yield: 15.24 g (84% of theory) of a colorless, hygroscopic solid
Water content: 7.3%
Elementary analysis (relative to anhydrous substance):
Cld: C, 46.85; H, 6.77; N, 15.18;
Fnd: C, 46.61; H, 6.95; N, 15.02;

5.86 g (16.25 mmol) of gadolinium oxide is added to 15 g (32.50 mmol) of the above-described acid, dissolved in 200 ml of water, and it is heated for 3 hours to 90° C. It is evaporated to the dry state (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 18.92 g (92% of theory) of a colorless, crystalline powder
Water content: 2.7%
Elementary analysis (relative to anhydrous substance):
Cld: C, 35.11; H, 4.58; N, 11.37; Gd, 25.54;
Fnd: C, 34.92; H, 4.71; N, 11.14; Gd, 25.33;

b) 1,4,7-Tris{1,4,7-tris-(carboxylatomethyl)-10-(3,6-diaza-2,5,8-trioxo-octane-1,8-diyl)-1,4,7,10-tetraazacyclododecane, Gd complex}-10-(N-2H,2H,4H,4H,5H,5H-3-oxa-perfluoro-tridecanoyl)-1,4,7,10-tetraazacyclododecane 16.94 g (27.5 mmol) of the Gd complex, described in Example 13a), of 10-(4-carboxy-2-oxo-3-azabutyl)-1,4,7,10-tetraazacyclododecane-1,4,7-triacetic acid, 2.83 g of sodium bromide (27.5 mmol) and 6.33 g (55 mmol) of N-hydroxysuccinimide are dissolved in 300 ml of dimethyl sulfoxide at 50° C. After cooling to room temperature, 11.35 g (55 mmol) of N,N'-dicyclohexylcarbodiimide is added and preactivated for 60 minutes. A solution of 5 g (4.59 mmol) of the title compound described in Example 1e) and 11.13 g (110 mmol) of triethylamine in 25 ml of water are added to the N-hydroxysuccinimide ester solution that is thus produced, and it is stirred overnight at room temperature.

The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-1 ultrafiltration membrane (cut-off/1,000 Da), and low-molecular components are removed. The retentate is then freeze-dried.

Yield: 11.16 g (92% of theory)
$H_2O$ content: 9.5%
Elementary analysis (relative to anhydrous substance):
Cld: C, 36.36; H, 4.35; N, 11.66; Gd, 17.85; F, 12.22;
Fnd: C, 36.28; H, 4.42; N, 11.58; Gd, 17.75; F, 12.14;

EXAMPLE 14 a) 22F,22F,22F,21F,21F,20F,20F,19F,19F,18F,18F,17F,17F, 16F, 15F,15F-Heptadecafluoro-12oxa-docosane-carboxylic acid-benzyl ester 18.83 g (53 mmol) of 11-bromoundecanoic acid benzyl ester is added in drops to a mixture of 10 g (21.55 mmol) of 1H,1H,2H,2H-perfluorododecanol and 0.73 g (2.15 mmol) of tetrabutylammonium hydrogen sulfate in 100 ml of 60% potassium hydroxide solution/50 ml of toluene while being stirred vigorously at 0° C. It is stirred for 1 hour at 0° C. 200 ml of toluene is added, the aqueous phase is separated and extracted twice with 50 ml of toluene each. The combined organic phases are dried on magnesium sulfate and concentrated by evaporation in a vacuum. The residue is chromatographed on silica gel (mobile solvent: hexane/dichloromethane/acetone=20:10:1).

Yield: 8.75 g (55% of theory) of a colorless, viscous oil
Elementary analysis:
Cld: C, 45.54; H, 4.23; F, 43.73;
Fnd: C, 45.48; H, 4.31; F, 43.68;

b) 22F,22F,22F,21F,21F,20F,20F,19F,19F,18F,18F,17F,17F, 16F, 15F,15F-Heptadecafluoro-12oxa-docosane-carboxylic acid 8 g (10.83 mmol) of the title compound of Example 14a) is dissolved in 200 ml of methanol, and 2 g of palladium catalyst (10% Pd/C) is added. It is hydrogenated overnight at room temperature. Catalyst is filtered out, and the filtrate is evaporated to the dry state in a vacuum.

Yield: 7.02 g (quantitative) of a vitreous, colorless solid
Elementary analysis:
Cld: C, 38.90; H, 3.89; F, 49.81;
Fnd: C, 38.75; H, 3.98; F, 49.72;

c) 1,4,7-Tris[N-(2-benzyloxycarbonylamino)-acetyl]-10-(N-22F,22F,22F,21F,21F,20F,20F,19F,19F,18F,18F,17F, 17F,16F,16F, 15F,15F-Heptadecafluoro-12oxa-docosanoyl)-1,4,7,10-tetraazacyclododecane 7 g (10.08 mmol) of the title compound of Example 14b) and 4.02 g (5.4 mmol) of the title compound of Example 14b) are dissolved in 100 ml of dimethylformamide, and 4.2 g (17 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: dichloromethane/acetone=15:1).

Yield: 6.17 (83% of theory) of a colorless, viscous oil
Elementary analysis:
Cld: C, 51.49; H, 5.13; N, 7.12; F, 23.47;
Fnd: C, 51.39; H, 5.20; N, 7.19; F, 23.38;

d) 1,4,7-Tris[N-(2-amino)-acetyl]-10-(N-22F,22F,22F,21F, 21F,20F,20F,19F,19F,18F,18F,17F,17F,16F,16F, 15F,15F-Heptadecafluoro-12-oxa-docosanoyl-1,4,7,10-tetraazacyclododecane, trihydrobromide 6 g (4.36 mmol) of the title compound of Example 14c) is dissolved in 50 ml of acetic acid and added in drops to a solution of 50 ml of hydrogen bromide in glacial acetic acid (33%) whose temperature is 60° C. It is stirred for 1 hour at 60° C. It is cooled to 0° C., and 1,000 ml of diethyl ether is slowly added in drops while being stirred. The deposited precipitate is filtered off, rewashed twice with 200 ml of ether and dried in a vacuum furnace (60° C.).

Yield: 4.93 g (93% of theory) of a cream-colored, crystalline solid
Elementary analysis:
Cld: C, 34.56; H, 4.56; N, 8.06; F, 26.55; Br, 19.70;
Fnd: C, 34.48; H, 4.70; N, 8.00; F, 26.48; Br, 19.46;

e) 1,4,7-Tris{1,4,7-tris-(N-carboxylatomethyl)-10-[N-(4,7-diaza-3,6,9-trioxo)-nonane-2,9-diyl]-1,4,7,10-tetraazacyclododecane, Gd complex-10-(N-22F,22F,22F, 21F,21F,20F,20F,19F,19F,18F,18F,17F,17F,16F,16F, 15F, 15F-heptadecafluoro-12-oxa-docosanoyl)-1,4,7,10-tetraazacyclododecane 13.98 g (22.9 mmol) of the Gd complex, described in Example 1f), of 10-(4-carboxy-1-methyl-2-oxo-3-azabutyl)-1,4,7,10-tetraazacyclododecane-1,4,7-triacetic acid, 2.36 g of sodium bromide (22.9 mmol) and 5.29 g (46 mmol) of N-hydroxysuccinimide are dissolved in 200 ml of dimethyl sulfoxide at 50° C. After cooling to room temperature, 9.49 g (46 mmol) of N,N'-dicyclohexylcarbodiimide is added and preactivated for 60 minutes. A solution of 4.5 g (3.7 mmol) of the title compound that is described in Example 14d) and 9.31 g (92 mmol) of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered off, and the filtrate is desalinated with an AMICON® YM-1 ultrafiltration membrane (cut-off 1,000 Da), and low-molecular components are removed. The retentate is then freeze-dried.

Yield: 9.78 g (94% of theory)
H$_2$O content: 6.8%
Elementary analysis (relative to anhydrous substance):
Cld: C, 39.31; H, 4.95; N, 10.96; F, 11.49; Gd, 16.78;
Fnd: C, 39.24; H, 5.02; N, 10.87; F, 11.41; Gd, 16.69;

EXAMPLE 15 a) N-(Hexyl)-perfluorooctanesulfonamide 50.21 g (100 mmol) of perfluorooctanesulfonyl fluoride is added in drops to a mixture of 10.62 g (105 mmol) of triethylamine and 10.12 g (100 mmol) of benzylamine at 80° C. while being stirred vigorously. It is stirred for 2 days at 80° C., the reaction mixture is mixed with 300 ml of water and extracted three times with ethyl acetate. The combined organic extracts are dried on sodium sulfate, filtered and concentrated by evaporation. The residue is chromatographed on silica gel (mobile solvent: dichloromethane/methanol=4:1).

Yield: 45.50 g (78% of theory) of a colorless liquid
Elementary analysis:
Cld: C, 28.83; H, 2.42; N, 2.40; S, 5.50; F, 55.37;
Fnd: C, 28.29; H, 2.39; N, 2.44; S, 5.55; F, 55.50;

b) N-(Hexyl)-(t-butyloxycarbonylmethyl)-perfluorooctylsulfonamide 22.13 g (37.94 mmol) of the title compound of Example 15a) and 15.73 g (113.8 mmol) of potassium carbonate are suspended in 200 ml of acetone, and 14.80 g (75.87 mmol) of bromoacetic acid-tert-butyl ester is added in drops at 60° C. It is stirred for 3 hours at 60° C. Salts are filtered out, and the filtrate is evaporated to the dry state in a vacuum. The residue is chromatographed on silica gel (mobile solvent: hexane/dichloromethane/acetone=10:10:1). After the product-containing fractions are concentrated by evaporation, the residue is recrystallized from methanol/ether.

Yield: 23.02 g (87% of theory) of a waxy, colorless solid
Elementary analysis:
Cld: C, 34.34; H, 3.47; N, 2.01; S, 4.60; F, 46.31;
Fnd: C, 34.31; H, 3.61; N, 1.97; S, 4.65; F, 46.25;

c) N-(Hexyl)-(perfluorooctylsulfonamide)-aminoacetic acid 20 g (28.43 mmol) of the title compound of Example 15b) is dissolved in 200 ml of trifluoroacetic acid and stirred overnight at room temperature. It is evaporated to the dry state in a vacuum. The residue is recrystallized from methanol/ether.

Yield: 16.74 g (91% of theory) of a colorless, crystalline solid
Elementary analysis:
Cld: C, 29.96; H, 2.51; N, 2.18; S, 5.00; F, 50.36;
Fnd: C, 29.87; H, 2.70; N, 2.05; S, 4.84; F, 50.17;

d) 1,4,7-Tris[N-(2-benzyloxycarbonylamino)-acetyl]-10-[N-acetyl-(2-amino-N-hexyl-N-perfluorooctylsulfonyl)]-1,4,7,10-tetraazacyclododecane 16 g (24.95 mmol) of the title compound of Example 15c) and 9.3 g (12.48 mmol) of the title compound of Example 1c) are dissolved in 200 ml of dimethylformamide, and 3.46 g (14 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: dichloromethane/acetone=15:1).

Yield: 13.5 g (79% of theory) of a colorless, viscous oil
Elementary analysis:
Cld: C, 47.37; H, 4.49; N, 8.18; F, 23.59; S, 2.34;
Fnd: C, 47.29; H, 4.57; N, 8.09; F, 23.48; S, 2.28;

e) 1,4,7-Tris[N-(2-amino)-acetyl]-10-(N-acetyl-(2-amino)-N-hexyl-N-perfluorooctyl-sulfonyl)]-1,4,7,10-tetraazacyclododecane, trihydrobromide 10 g (7.30 mmol) of the title compound of Example 15d) is dissolved in 100 ml of acetic acid and added in drops to a solution of 150 ml of hydrogen bromide in glacial acetic acid (33%) whose temperature is 60° C. It is stirred for 1 hour at 60° C. It is cooled to 0° C., and 1,300 ml of diethyl ether is slowly added in drops while being stirred. The deposited precipitate is filtered off, rewashed twice with 150 ml of ether and dried in a vacuum furnace (60° C.).

Yield: 8.48 g (96% of theory) of a cream-colored, crystalline solid
Elementary analysis:
Cld: C, 29.79; H, 3.83; N, 9.26; F, 26.70; Br, 19.82; S, 2.65;
Fnd: C, 29.68; H, 3.95; N, 9.20; F, 26.62; Br, 19.73; S, 2.58;

f) 1,4,7-Tris[1,4,7-tris[N-carboxylatomethyl)-10-(3,6-diaza-2,5-dioxo-octane-1,8-diyl)-1,4,7,10-tetraazacyclododecane, Gd complex]-10-[2-(N-acetyl-(2-amino)-N-hexyl-N-perfluorooctylsulfonyl)]-1,4,7,10-tetraazacyclododecane 15.62 g (24.8 mmol) of the Gd complex, described in Example 1f), of 10-(4-carboxy-1-methyl-2-oxo-3-azabutyl)-1,4,7,10-tetraazacyclododecane-1,4,7-triacetic acid, 2.55 g of sodium bromide (24.8 mmol) and 5.75 g (50 mmol) of N-hydroxysuccinimide are dissolved in 200 ml of dimethyl sulfoxide at 50° C. After cooling to room temperature, 10.32 g (50 mmol) of N,N'-dicyclohexylcarbodiimide is added and preactivated for 60 minutes.

A solution of 5 g (4.13 mmol) of the title compound that is described in Example 15e) and 10.12 g (100 mmol) of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered off, and the filtrate is desalinated with an AMICON® YM-1 ultrafiltration membrane (cut-off 1,000 Da), and low-molecular components are removed. The retentate is then freeze-dried.

Yield: 10.6 g (93% of theory) $H_2O$ content: 11.0%
Elementary analysis (relative to anhydrous substance):
Cld: C, 36.56; H, 4.42; N, 11.67; Gd, 17.09; F, 11.70; S, 1.16;
Fnd: C, 36.48; H, 4.50; N, 11.61; Gd, 16.98; F, 11.61; S, 1.13;

EXAMPLE 16 a) 1,4,7-Tris(N-carboxylatomethyl)-10-[N-(6-aza-8-hydroxy-3-oxa-5-oxo)-nonan-9-yl-acid]-1,4,7,10-tetraazacyclododecane, Gd complex 36 g (355.5 mmol) of triethylamine is added to a solution of 23.21 g (200 mmol) of diglycolic acid anhydride and 102 g (177.76 mmol) of 10-[3-amino-2-hydroxypropyl]-1,4,7-tris-carboxymethyl-1,4,7,10-tetraazacyclododecane-gadolinium complex in 1,000 ml of formamide. It is stirred overnight at room temperature. 8,000 ml of acetone is dripped into this solution while being stirred, the deposited precipitate is filtered off, washed with acetone and dried in a vacuum. The material that is thus dried is dissolved in 2,000 ml of water and set at pH 3.2 with 2N hydrochloric acid, then it is freeze-dried. The freeze-dried powder is dissolved in very little water and placed on an RP18 column. It is chromatographed with a mobile solvent mixture that consists of water/tetrahydrofuran (gradient). The product-containing fractions are evaporated to the dry state in a vacuum, and the residue is recrystallized from 2-propanol. After drying in a vacuum furnace at 120° C. (24 hours), 100.54 g (82% of theory) of the title compound is obtained as a colorless, crystalline powder.

Water content: 3.1%
Elementary analysis (relative to anhydrous substance):
Cld: C, 36.57; H, 4.97; N, 10.15; Gd, 22.80;
Fnd: C, 36.41; H, 5.12; N, 9.96; Gd, 22.59;

b) 1,4,7-Tris{1,4,7-tris(N-carboxylatomethyl)-10-[N-4,10-diaza-2-hydroxy-5,8,12-trioxo-7-oxa-dodecane-1,12-diyl], Gd complex}-10-(N-2H,2H,4H,4H,5H,5H-3-oxa-perfluorotridecanoyl)-1,4,7,10-tetraazacyclododecane 19 g (27.52 mmol) of the Gd complex that is described in Example 16a) and 2.81 g of sodium bromide (27.52 mmol) and 3.17 g (27.52 mmol) of N-hydroxysuccinimide are dissolved in 250 ml of dimethyl sulfoxide at 50° C. After cooling to room temperature, 6.19 g (30 mmol) of N,N'-dicyclohexylcarbodiimide is added and preactivated for 60 minutes. A solution of 5 g (4.59 mmol) of the title compound that is described in Example 1e) and 6.07 g (60 mmol) of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered off, and the filtrate is desalinated with an AMICON® YM-1 ultrafiltration membrane (cut-off 1,000 Da), and low-molecular components are removed. The retentate is then freeze-dried.

Yield: 12.35 g (94% of theory)

$H_2O$ content: 9.6%
Elementary analysis (relative to anhydrous substance):
Cld: C, 37.34; H, 4.58; N, 10.76; Gd, 16.48; F, 11.28;
Fnd: C, 37.25; H, 4.71; N, 10.60; Gd, 16.37; F, 11.13;

EXAMPLE 17

1,4,7-Tris{1,4,7-tris(N-carboxylatomethyl)-10-[N-(4-aza-2-hydroxy-5,9-dioxo-7-oxa)-nonane-1,9-diyl]-1,4,7,10-tetraazacyclododecane, Gd complex}-10-2H,2H,4H,4H,5H,5H-3-oxa-perfluoro-tridecanoyl)-1,4,7,10-tetraazacyclododecane 19 g (27.52 mmol) of the Gd complex that is described in Example 16a) and 2.83 g of sodium bromide (27.52 mmol) are dissolved in 200 ml of dimethyl sulfoxide at 50° C. After cooling to room temperature, 3.1 g (4.59 mmol) of the title compound that is described in Example 4b) and 9.89 g (40 mmol) of 2-ethoxy-1-ethoxycarbonyl-1,2-dihydroquinoline are added and stirred overnight at room temperature. The suspension that is obtained is then mixed with sufficient acetone until complete precipitation occurs, the precipitate is suctioned off, dried, taken up in water and desalinated with an AMICON® YM-1 ultrafiltration membrane (cut-off 1,000 Da), and low-molecular components are removed. The retentate is then freeze-dried.

Yield: 11.37 g (92% of theory)
$H_2O$ content: 8.9%
Elementary analysis (relative to anhydrous substance):
Cld: C, 37.04; H, 4.53; N, 9.89; Gd, 17.53; F, 12.00;
Fnd: C, 36.95; H, 4.65; N, 9.78; Gd, 17.37; F, 11.87;

EXAMPLE 18 a) 1,4,7-Tris[N-(2-benzyloxycarbonylamino)-acetyl]-10-[N-acetyl-(2-amino-N-ethyl-N-perfluorooctylsulfonyl)]-1,4,7,10-tetraazacyclododecane 20 g (39.48 mmol) of the title compound of Example 12b) and 10.99 g (14.74 mmol) of the title compound of Example 1c) are dissolved in 200 ml of dimethylformamide, and 3.46 g (14 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: dichloromethane/acetone=15:1).

Yield: 16.06 g (83% of theory) of a colorless, viscous oil
Elementary analysis:
Cld: C, 45.74; H, 4.07; N, 8.53; F, 24.60; S, 2.44;
Fnd: C, 45.68; H, 4.19; N, 8.48; F, 24.45; S, 2.36;

b) 1,4,7-Tris[N-(2-amino)-acetyl]-10-[N-acetyl-(2-amino-N-ethyl-N-perfluorooctyl-sulfonyl)]-1,4,7,10-tetraazacyclododecane, trihydrobromide 10 g (7.62 mmol) of the title compound of Example 18a) is dissolved in 100 ml of acetic acid and added in drops to a solution of 150 ml of hydrogen bromide in glacial acetic acid (33%) whose temperature is 60° C. It is stirred for 1 hour at 60° C. It is cooled to 0° C., and 1,600 ml of diethyl ether is slowly added in drops while being stirred. The deposited precipitate is filtered off, rewashed twice with 200 ml of ether and dried in a vacuum furnace (60° C.).

Yield: 8 g (91% of theory) of a cream-colored, crystalline solid
Elementary analysis:
Cld: C, 27.08; H, 3.32; N, 9.72; F, 28.00; Br, 20.78; S, 2.78;
Fnd: C, 26.94; H, 3.42; N, 9.63; F, 27.91; Br, 20.46; S, 2.74;

c) 1,4,7-Tris{N-3,9-bis(N-t-butyloxycarbonylmethyl)-6-[N-(3-aza-2,5-dioxo-pentane1,5-diyl]-3,6,9-triazaundecane- 1,11-dioic acid-di-t-butyl ester}-10-[N-acetyl-(2-amino-N-ethyl-N-perfluorooctylsulfonyl)]-1,4,7,10-tetraazacyclododecane 5.98 g (52 mmol) of N-hydroxysuccinimide and 10.73 g (52 mmol) of N,N'-dicyclohexylcarbodiimide are added to 16.04 g (26 mmol) of sym-DTPA-tetra-tert-butyl ester, dissolved in 200 ml of dimethylformamide, at 0° C., and it is stirred for one hour at this temperature. Then, it is stirred for 3 hours at room temperature. 5 g (4.34 mmol) of the title compound of Example 18b) and 10.12 g (100 mmol) of triethylamine are added to this solution. It is stirred for 24 hours at room temperature. The solution is evaporated to the dry state, and the residue is taken up in 300 ml of dichloromethane. Dicyclohexylurea is filtered off, and the filtrate is washed twice with 150 ml of 5% aqueous sodium carbonate solution. The organic phase is dried on magnesium sulfate and evaporated to the dry state in a vacuum. The residue is chromatographed on silica gel (mobile solvent: dichloromethane/methanol=20:1).

Yield: 11.68 g (95% of theory) of a colorless, viscous oil
Elementary analysis:
Cld: C, 49.20; H, 6.55; N, 11.38; F, 11.40; S, 1.13;
Fnd: C, 49.10; H, 6.70; N, 11.31; F, 11.29; S, 1.06;

d) 1,4,7-Tris{N-3,9-bis(carboxylatomethyl)-6-[N-3-aza-2,5-dioxo-pentane-1,5-diyl]-3,6,9-triazaundecane-1-carboxylato-11-acid, Gd complex, sodium salt}-10-[N-acetyl-(2-amino-N-ethyl-N-perfluorooctylsulfonyl)]-1,4,7,10-tetraazacyclododecane 11 g (3.88 mmol) of the title compound of Example 18c) is dissolved in 200 ml of trifluoroacetic acid and stirred for 12 hours at room temperature. It is evaporated to the dry state in a vacuum. The residue is dissolved in 200 ml of water and set at pH 4 with 10% aqueous sodium hydroxide solution. Then, 2.11 g (5.82 mmol) of gadolinium oxide is added, and it is stirred for 2 hours at 70° C. It is cooled to room temperature and set at pH 7.2 with 10% aqueous sodium hydroxide solution. The solution is mixed with 2 g of activated carbon, stirred for 1 hour at room temperature and filtered. The filtrate is filled in an ultrafiltration cell and dialyzed (AMICON® YM-1 (cut-off 1,000 Da)). Dialysis is performed until the eluate has reached a conductivity of 10 μS. Then, the contents of the ultrafiltration cell are freeze-dried.

Yield: 9.67 g (97% of theory) of a colorless, amorphous powder
Water content: 10.1%
Elementary analysis (relative to anhydrous substance):
Cld: C, 31.84; H, 3.38; N, 9.28; F, 12.59; S, 1.25; Gd, 20.24; Na, 2.96;
Fnd: C, 31.70; H, 3.51; N, 9.14; F, 12.45; S, 1.16; Gd, 20.11; Na, 2.73;

EXAMPLE 19

1,4,7-Tris{1,4,7-tris(N-carboxylatomethyl)-10-[N-(4,7-diaza-3,6,9-trioxo)-nonane-2,9-diyl]-1,4,7,10-tetraazacyclododecane, Gd complex}-10-[N-acetyl-(2-amino-N-ethyl-N-perfluoro-octylsulfonyl)]-1,4,7,10-tetraazacyclododecane 16.38 g (26.0 mmol) of the Gd complex, described in Example 1f), of 10-(4-carboxy-1-methyl-2-oxo-3-azabutyl)-1,4,7,10-tetraazacyclododecane-1,4,7-triacetic acid, 2.68 g of sodium bromide (26 mmol) and 5.98 g (52 mmol) of N-hydroxysuccinimide are dissolved in 200 ml of dimethyl sulfoxide at 50° C. After cooling to room temperature, 10.73 g (52 mmol) of N,N'-dicyclohexylcarbodiimide is added and preactivated for 60 minutes. A solution of 5 g (4.34 mmol) of the title compound that is described in Example 18b) and 10.12 g (100 mmol) of triethylamine in 25 ml of water are added to the N-hydroxysuccinimide ester solution that is thus produced and stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-1 ultrafiltration membrane (cut-off 1,000 Da), and low-molecular components are removed. The retentate is then freeze-dried.

Yield: 11.08 g (93% of theory)
H$_2$O content: 6.8%
Elementary analysis (relative to anhydrous substance):
Cld: C, 36.31; H, 4.37; N, 11.73; F, 11.76; S, 1.17; Gd, 17.18;
Fnd: C, 36.25; H, 4.46; N, 11.68; F, 11.70; S, 1.10; Gd, 17.09;

EXAMPLE 20 a) 1,4,7-Tris{N-[3-aza-(N-benzyloxycarbonyl)-5-oxo]-pent-5-yl acid}-10-(N-2H,2H,4H,4H,5H,5H-3-oxa-perfluoro-tridecanoyl)-1,4,7,10-tetraazacyclododecane 9.28 (45 mmol) of N,N'-dicyclohexylcarbodiimide is added to 11.85 g (44.35 mmol) of N-(benzyloxycarbonyl)-aminodiacetic acid, dissolved in 200 ml of tetrahydrofuran, and it is stirred for 3 hours at room temperature. Precipitated dicyclohexylurea is filtered out, and 5 g (7.39 mmol) of the title compound of Example 4b), 15.18 g (150 mmol) of triethylamine and 200 mg of 4-(dimethylamino)pyridine are added to the filtrate. It is heated for 12 hours to 50° C. It is evaporated to the dry state, the residue is taken up in 300 ml of 10% aqueous citric acid solution and extracted 3 times with 250 ml of chloroform each. The combined organic phases are dried on magnesium sulfate and evaporated to the dry state in a vacuum. The residue is chromatographed on silica gel (mobile solvent: chloroform/methanol=5:1, (+1% glacial acetic acid)).

Yield: 8.52 g (81% of theory) of a colorless solid
Elementary analysis:
Cld: C, 47.23; H, 4.10; N, 6.88; F, 22.68;
Fnd: C, 47.19; H, 4.21; N, 6.74; F, 22.57;

b) 1,4,7-Tris[N-(3-aza-5-oxo)-pent-5-yl-acid]-10-(N-2H,2H,4H,4H,5H,5H-3-oxa-perfluorotridecanoyl)-1,4,7,10-tetraazacyclododecane, trihydrobromide 8 g (5.62 mmol) of the title compound of Example 20a) is dissolved in 80 ml of acetic acid and added in drops to a solution of 150 ml of hydrogen bromide in glacial acetic acid (33%) whose temperature is 60° C. It is stirred for 1 hour at 60° C. It is cooled to 0° C., and 1,200 ml of diethyl ether is slowly added in drops while being stirred. The deposited precipitate is filtered off, rewashed twice with 150 ml of ether and dried in a vacuum furnace (60° C.).

Yield: 6.75 g (95% of theory) of a cream-colored, crystalline solid
Elementary analysis:
Cld: C, 30.40; H, 3.43; N, 7.75; F, 25.54; Br, 18.96;
Fnd: C, 30.31; H, 3.51; N, 7.68; F, 25.47; Br, 18.74;

c) 1,4,7-Tris{1,4,7-tris(N-carboxylatomethyl)-10-[N-(4,7-diaza-7-N-carboxymethyl-3,6,9-trioxo)-nonane-2,9-diyl]-1,4,7,10-tetraazacyclododecane, Gd complex, monosodium salt}-10-(N-2H,2H,4H,4H,5H,5H-3-oxa-perfluorotridecanoyl)-1,4,7,10-tetraazacyclododecane 19.92 g (31.63 mmol) of the Gd complex, described in Example 1f), of 10-(4-carboxy-1-methyl-2-oxo-3-azabutyl)-1,4,7,10-tetraazacyclododecane-1,4,7-triacetic acid, 3.25 g of sodium bromide (31.63 mmol) and 3.64 g (31.63 mmol) of N-hydroxysuccinimide are dissolved in 250 ml of dimethyl sulfoxide at 50° C. After cooling to room temperature, 6.53 g (31.63 mmol) of N,N'-dicyclohexylcarbodiimide is added and preactivated for 60 minutes. A solution of 5 g (3.95 mmol) of the title compound that is described in Example 20b) and 10.12 g (100 mmol) of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered off, and the filtrate is desalinated with an AMICON® YM-1 ultrafiltration membrane (cut-off 1,000 Da), and low-molecular components are removed. The retentate is set at pH 7.2 with 1N sodium hydroxide solution and then freeze-dried.

Yield: 10.39 g (90% of theory)
$H_2O$ content: 10.1%
Elementary analysis (relative to anhydrous substance):
Cld: C, 36.59; H, 4.14; N, 10.55; F, 11.05; Gd, 16.15; Na, 2.36;
Fnd: C, 36.50; H, 4.28; N, 10.47; F, 10.95; Gd, 16.03; Na, 2.14;

EXAMPLE 21 a) 1,4,7-Tris[N-(2-benzyloxycarbonylamino-aspartic acid-benzyl ester-4-amide)]-10-[(N-2H,2H,4H,4H,5H,5H-3-oxa-perfluoro-tridecanoyl)]-1,4,7,10-tetraazacyclododecane 5 g (7.39 mmol) of the title compound of Example 4b) and 15.72 g (44 mmol) of N-(benzyl-oxycarbonyl-aspartic acid-1-benzyl ester are dissolved in 100 ml of dimethylformamide, and 19.8 g (80 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: dichloromethane/acetone=20:1).

Yield: 9.64 g (77% of theory) of a colorless, viscous oil
Elementary analysis:
Cld: C, 54.58; H, 4.52; N, 5.79; F, 19.06;
Fnd: C, 54.48; H, 4.61; N, 5.71; F, 18.94;

b) 1,4,7-Tris[N-(2-amino-aspartic acid-4-amide)]-10-(N-2H,2H,4H,4H,5H,5H-3-oxa-perfluoro-tridecanoyl)-1,4,7,10-tetraazacyclododecane 8 g (4.72 mmol) of the title compound of Example 21a) is dissolved in 80 ml of acetic acid and added in drops to a solution of 150 ml of hydrogen bromide in glacial acetic acid (33%) whose temperature is 60° C. It is stirred for 1 hour at 60° C. It is cooled to 0° C., and 1,600 ml of diethyl ether is slowly added in drops while being stirred. The deposited precipitate is filtered off, rewashed twice with 150 ml of ether and dried in a vacuum furnace (60° C.).

Yield: 5.67 g (95% of theory) of a cream-colored, crystalline solid
Elementary analysis:
Cld: C, 30.40; H, 3.43; N, 7.75; F, 25.54; Br, 18.96;
Fnd: C, 30.28; H, 3.51; N, 7.69; F, 25.47; Br, 18.87;

c) 1,4,7-Tris{1,4,7-tris(N-carboxylatomethyl)-10-[N-(4,7-diaza-8-carboxy-3,6,9-trioxo)-decane-2,10-diyl]-1,4,7,10-tetraazacyclododecane, Gd complex, monosodium salt}-10-2H,2H,4H,4H,5H,5H-3-oxo-perfluorotridecanoyl)-1,4,7,10-tetraazacyclododecane 14.94 g (23.7 mmol) of the Gd complex, described in Example 1f), of 10-(4-carboxy-1-methyl-2-oxo-3-azabutyl)-1,4,7,10-tetraazacyclododecane-1,4,7-triacetic acid, 2.44 g of sodium bromide (23.7 mmol) and 2.73 g (23.7 mmol) of N-hydroxysuccinimide are dissolved in 200 ml of dimethyl sulfoxide at 50° C. After cooling to room temperature, 4.89 g (23.7 mmol) of N,N'-dicyclohexylcarbodiimide is added and preactivated for 60 minutes. A solution of 5 g (3.95 mmol) of the title compound that is described in Example 21b) and 10.12 g (100 mmol) of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered off, and the filtrate is desalinated with an AMICON® YM-1 ultrafiltration membrane (cut-off 1,000 Da), and low-molecular components are removed. The retentate is set at pH 7.2 with 1N sodium hydroxide solution and then freeze-dried.

Yield: 10.73 g (93% of theory)
$H_2O$ content: 8.5%
Elementary analysis (relative to anhydrous substance):
Cld: C, 36.59; H, 4.14; N, 10.55; F, 11.05; Gd, 16.15; Na, 2.36;
Fnd: C, 36.50; H, 4.23; N, 10.48; F, 10.96; Gd, 16.07; Na, 2.13;

EXAMPLE 22 a) 1,4,7-Tris[2,6-bis(benzyloxycarbonylamino)-hexanoyl]-10-(N-2H,2H,4H,4H,5H,5H-3-oxa-perfluorotridecanoyl)-1,4,7,10-tetraazacyclododecane 5 g (7.39 mmol) of the title compound of Example 4b) and 15.33 g (37 mmol) of di-Z-lysine are dissolved in 150 ml of dimethylformamide, and 11.13 g (45 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: dichloromethane/acetone=25:1).

Yield: 10.34 g (75% of theory) of a colorless, viscous oil
Elementary analysis:
Cld: C, 55.36; H, 5.24; N, 7.51; F, 17.31;
Fnd: C, 55.28; H, 5.31; N, 7.43; F, 17.23;

b) 1,4,7-Tris(2,6-diamino-hexanoyl)-10-N-2H,2H,4H,4H,5H,5H-3-oxa-perfluoro-tridecanoyl)-1,4,7,10-tetraazacyclododecane, hexahydrobromide 8 g (4.29 mmol) of the title compound of Example 22a) is dissolved in 80 ml of acetic acid and added in drops to a solution of 150 ml of hydrogen bromide in glacial acetic acid (33%) whose temperature is 60° C. It is stirred for 1 hour at 60° C. It is cooled to 0° C., and 1,600 ml of diethyl ether is slowly added in drops while being stirred. The deposited precipitate is filtered off, rewashed twice with 200 ml of ether and dried in a vacuum furnace (60° C.).

Yield: 5.38 g (96% of theory) of a cream-colored, crystalline solid
Elementary analysis:
Cld: C, 34.93; H, 5.17; N, 10.72; F, 24.72; Br, 18.34;
Fnd: C, 34.87; H, 5.25; N, 10.65; F, 24.57; Br, 18.15;

c) 1,4,7-Tris{2,6-bis<amino-[(3-aza-1,4-dioxohexane-1,5-diyl)-10-(N-1,4,7,10-tetraaza-cyclododecane-1,4,7-tris (carboxylatomethyl), Gd-complex]>-hexanoyl}-10-(N-2H,2H,4H,4H,5H,5H-3-oxa-perfluoro-tridecanoyl)-1,4,7,10-tetraazacyclododecane, hexahydrobromide 28.97 g (46 mmol) of the Gd complex, described in Example 1f), of 10-(4-carboxy-1-methyl-2-oxo-3-azabutyl)-1,4,7,10-tetraazacyclododecane-1,4,7-triacetic acid, 4.7 g of sodium bromide (46 mmol) and 10.59 g (92 mmol) of N-hydroxysuccinimide are dissolved in 300 ml of dimethyl sulfoxide at 50° C. After cooling to room temperature, 18.98 g (92 mmol) of N,N'-dicyclohexylcarbodiimide is added and preactivated for 60 minutes. A solution of 5 g (3.83 mmol) of the title compound that is described in Example 22b) and 20.34 g (200 mmol) of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered off, and the filtrate is desalinated with an AMICON® YM-1 ultrafiltration membrane (cut-off 1,000 Da), and low-molecular components are removed. The retentate is set at pH 7.2 with 1N sodium hydroxide solution and then freeze-dried.

Yield: 16.49 g (91% of theory)
$H_2O$ content: 10.2%
Elementary analysis (relative to anhydrous substance):
Cld: C, 38.59; H, 4.88; N, 11.84; F, 6.83; Gd, 19.94;
Fnd: C, 38.50; H, 4.97; N, 11.68; F, 6.70; Gd, 19.82;

EXAMPLE 23 a) 1,4,7,-Tris[N-(3-benzyloxycarbonylaminoglutaric acid-monoamide)]-10-(N-2H-2H-4H,4H,5H,5H-3-oxa-perfluoro-tridecanoyl)-1,4,7,10-tetraazacyclododecane 9.28 g (45 mmol) of dicyclohexylcarbodiimide is added to 12.47 g (44.35 mmol) of 3-[N-(benzyloxycarbonyl)amino]-glutaric acid, dissolved in 200 ml of tetrahydrofuran, and it is stirred for 3 hours at room temperature. Precipitated dicyclohexylurea is filtered out, and 5 g (7.39 mmol) of the title compound of Example 4b), 15.18 g (150 mmol) of triethylamine and 200 mg of 4-(dimethylamino)-pyridine are added to the filtrate. It is heated for 12 hours to 50° C. It is evaporated to the dry state, the residue is taken up in 300 ml of 10% aqueous citric acid solution and extracted 3 times with 250 ml of chloroform each. The combined organic phases are dried on magnesium sulfate and evaporated to the dry state in a vacuum. The residue is chromatographed on silica gel (mobile solvent: chloroform/methanol=5:1, (+1% glacial acetic acid).

Yield: 8.57 g (81% of theory) of a colorless solid
Elementary analysis:
Cld: C, 48.27; H, 4.53; N, 6.68; F, 22.00;
Fnd: C, 48.10; H, 4.71; N, 6.47; F, 21.81;

b) 1,4,7,-Tris(N-(3-amino-glutaric acid-monoamide)]-10-(N-2H-2H-4H,4H,5H,5H-3-oxa-perfluoro-tridecanoyl)-1,4,7,10-tetraazacyclododecane 5 g (3.41 mmol) of the title compound of Example 23a) is dissolved in 50 ml of acetic acid and added in drops to a solution of 100 ml of hydrogen bromide in glacial acetic acid (33%) whose temperature is 60° C. It is stirred for 1 hour at 60° C. It is cooled to 0° C., and 1,000 ml of diethyl ether is slowly added in drops while being stirred. The deposited precipitate is filtered off, rewashed twice with 100 ml of ether and dried in a vacuum furnace (60° C.).

Yield: 4.19 g (94% of theory) of a cream-colored, crystalline solid
Elementary analysis:
Cld: C, 32.18; H, 3.78; N, 7.50; F, 24.72; Br, 18.35;
Fnd: C, 32.10; H, 3.94; N, 7.35; F, 24.51; Br, 18.14;

c) 1,4,7-Tris{1,4,7-tris(N-carboxylatomethyl)-10-[N-(4,7-diaza-8-carboxymethyl-3,6,10-trioxo)-decane-2,10-diyl]-1,4,7,10-tetraazacyclododecane, Gd complex, monosodium salt}- 10-(N-2H-2H-4H,4H,5H,5H-3-oxa-perfluoro-tridecanoyl)-1,4,7,10-tetraazacyclododecane 11.57 g (18.4 mmol) of the Gd complex, described in Example 1f), of 10-(4-carboxy-1-methyl-2-oxo-3-azabutyl)-1,4,7,10-tetraazacyclododecane-1,4,7-triacetic acid, 1.89 g of sodium bromide (18.4 mmol) and 2.12 g (18.4 mmol) of n-hydroxysuccinimide are dissolved in 150 ml of dimethyl sulfoxide at 50° C. After cooling to room temperature, 3.80 g (18.4 mmol) of N,N'-dicyclohexylcarbodiimide is added and preactivated for 60 minutes. A solution of 4 g (3.06 mmol) of the title compound that is described in Example 23b) and 4.05 g (40 mmol) of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered off, and the filtrate is desalinated with an AMICON® YM-1 ultrafiltration membrane (cut-off 1,000 Da), and low-molecular components are removed. The retentate is set at pH 7.2 with 1N sodium hydroxide solution and then freeze-dried.

Yield: 8.62 g (95% of theory)
$H_2O$ content: 9.6%
Elementary analysis (relative to anhydrous substance):
Cld: C, 37.28; H, 4.28; N, 10.40; F, 10.90; Gd, 15.93; Na, 2.33;
Fnd: C, 37.14; H, 4.41; N, 10.25; F, 10.73; Gd, 15.75; Na, 2.10;

EXAMPLE 24 a) 4-[(N-Ethyl-N-perfluorooctylsulfonyl)-aminomethyl]-benzoic acid methyl ester 20 g (37.94 mmol) of N-ethylperfluorooctylsulfonamide and 15.73 g (113.8 mmol) of potassium carbonate are suspended in 200 ml of acetone, and (75.87 mmol) of 4-(bromomethyl)-benzoic acid methyl ester is added in drops at 60° C. It is stirred for 3 hours at 60° C. Salts are filtered out, and the filtrate is evaporated to the dry state in a vacuum. The residue is chromatographed on silica gel (mobile solvent: hexane/dichloromethane/acetone=10:10:1). After the product-containing fractions are concentrated by evaporation, the residue is recrystallized from methanol/ether.

Yield: 22.80 g (89% of theory) of a waxy, colorless solid
Elementary analysis:
Cld: C, 33.79; H, 2.09; F, 47.82; N, 2.07; S, 4.75;
Fnd: C, 33.61; H, 2.28; F, 47.65; N, 2.01; S, 4.68;

b) 4-[(N-Ethyl-N-perfluorooctylsulfonyl)-amino-methyl]-benzoic acid 22 g (32.58 mmol) of the title compound of Example 24a) is dissolved in a mixture of 100 ml of $H_2O$/200 ml of ethanol, and 4 g (100 mmol) of sodium hydroxide is added. It is heated for 5 hours to 60° C. It is evaporated to the dry state in a vacuum, and the residue is taken up in 400 ml of 5% aqueous hydrochloric acid. It is extracted twice with 250 ml of dichloromethane each. The organic phase is dried on magnesium sulfate and evaporated to the dry state in a vacuum, and the residue is recrystallized from diethyl ether/n-hexane.

Yield: 21.12 g (98% of theory) of colorless, waxy crystals
Elementary analysis:
Cld: C, 32.69; H, 1.83; N, 2.12; F, 48.84; S, 4.85;
Fnd: C, 32.47; H, 2.02; N, 2.02; F, 48.65; S, 4.68;

c) 1,4,7-Tris[N-(2-benzyloxycarbonylamino)-acetyl]-10-{[4-(N-ethyl-N-perfluoro-octylsulfonyl)-aminomethyl]-benzoyl}-1,4,7,10-tetraazacyclododecane 21 g (31.75 mmol) of the title compound of Example 24b) and 11.86 g (15.9 mmol) of the title compound of Example 1c) are dissolved in 200 ml of dimethylformamide, and 8.66 g (35 mmol) of 2-ethoxy-1-ethoxycarbonyl-1,2- dihydroquinoline is added at 0° C. It is stirred for 24 hours at room temperature. It is evaporated to the dry state in a vacuum, and the residue is chromatographed on silica gel (mobile solvent: dichloromethane/acetone=15:1).

Yield: 18.7 g (85% of theory) of a colorless, viscous oil
Elementary analysis:
Cld: C, 48.42; H, 4.14; N, 8.07; F, 23.25; S, 2.31;
Fnd: C, 48.25; H, 4.02; N, 7.92; F, 23.04; S, 2.18;

d) 1,4,7-Tris-[N-(2-amino)-acetyl]-10-{4-[(N-ethyl-N-perfluorooctylsulfonyl)-amino-methyl]-benzoyl}-1,4,7,10-tetraazacyclododecane, trihydrobromide 10 g (7.2 mmol) of the title compound of Example 24c) is dissolved in 100 ml of acetic acid and added in drops to a solution of 100 ml of hydrogen bromide in glacial acetic acid (33%) whose temperature is 60° C. It is stirred for 1 hour at 60° C. It is cooled to 0° C., and 1,600 ml of diethyl ether is slowly added in drops while being stirred. The deposited precipitate is filtered off, rewashed twice with 200 ml of ether and dried in a vacuum furnace (60° C.).

Yield: 8.59 g (97% of theory) of a cream-colored, crystalline solid
Elementary analysis:
Cld: C, 31.26; H, 3.44; N, 9.11; F, 26.27; S, 2.61; Br, 19.50;
Fnd: C, 31.11; H, 3.60; N, 9.02; F, 26.09; S, 2.48; Br, 19.27;

e) 1,4,7-Tris{1,4,7-tris(N-carboxylatomethyl)-10-[N-(4,7-diaza-3,6,9-trioxo)-nonane-1,9-diyl]-Gd-complex}-10-{4-[(N-ethyl-N-perfluorooctylsulfonyl)-aminomethyl]-benzoyl}-1,4,7,10-tetraazacyclododecane 15.74 g (25 mmol) of the Gd complex, described in Example 1f), of 10-(4-carboxy-1-methyl-2-oxo-3-azabutyl)-1,4,7,10-tetraazacyclododecane-1,4,7-triacetic acid, 2.57 g of sodium bromide (25 mmol) and 5.75 g (18.4 mmol) of N-hydroxysuccinimide are dissolved in 200 ml of dimethyl sulfoxide at 50° C. After cooling to room temperature, 10.32 g (50 mmol) of N,N'-dicyclohexylcarbodiimide is added and preactivated for 60 minutes. A solution of 5 g (4.07 mmol) of the title compound that is described in Example 24d) and 10.12 g (100 mmol) of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-1 ultrafiltration membrane (cut-off 1,000 Da), and low-molecular components are removed. The retentate is set at pH 7.2 with 1N sodium hydroxide solution and then freeze-dried.

Yield: 10.91 g (95% of theory)
H$_2$O content: 9.6%
Elementary analysis (relative to anhydrous substance):
Cld: C, 37.88; H, 4.39; N, 11.42; F, 11.45; S, 1.14; Gd, 16.72;
Fnd: C, 37.64; H, 4.61; N, 11.27; F, 11.28; S, 1.08; Gd, 16.58;

EXAMPLE 25 a) 1,4,7-Tris[N-(2-benzyloxycarbonylamino)-acetyl]-10-N-[(11-t-butyloxy-carbonylamino)-undecanoyl]-1,4,7,10-tetraazacyclododecane 10 g (13.41 mmol) of the title compound of Example 1c) and 8.10 g (26.8 mmol) of 11-N-(tert-butoxycarbonyl)-aminoundecanoic acid are dissolved in 200 ml of dimethylformamide, and 9.89 g (40 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: dichloromethane/acetone=15:1).

Yield: 18.7 g (85% of theory) of a colorless, viscous oil
Elementary analysis:
Cld: C, 63.02; H, 7.44; N, 10.89;
Fnd: C, 62.90; H, 7.61; N, 10.63;

b) 1,4,7-Tris[N-(2-benzyloxycarbonylamino)-acetyl]-10-N-(11-aminoundecanoyl)-1,4,7,10-tetraazacyclododecane 12 g (11.66 mmol) of the title compound of Example 25a) is dissolved in 180 ml of trifluoroacetic acid and stirred overnight at room temperature. It is evaporated to the dry state in a vacuum. The residue is taken up in 200 ml of 2N sodium hydroxide solution and extracted twice with 150 ml of dichloromethane each. The combined organic phases are dried on magnesium sulfate and concentrated by evaporation in a vacuum. The residue is chromatographed on silica gel (mobile solvent: dichloromethane/methanol=15:1, (+2 triethylamine)).

Yield: 10.18 g (94% of theory) of a colorless solid
Elementary analysis:
Cld: C, 63.34; H, 7.38; N, 12.06;
Fnd: C, 63.15; H, 7.57; N, 11.84;

c) 1,4,7-Tris[N-(2-benzyloxycarbonylamino)-acetyl]-10-N-{undecanoyl-<11-amino-N-[acetyl-(2-amino-N-ethyl-N-perfluorooctylsulfonyl)]>}-1,4,7,10-tetraazacyclododecane 11.70 g (20 mmol) of the title compound of Example 12b) and 2.30 g (20 mmol) of N-hydroxysuccinimide are dissolved in 100 ml of dimethylformamide and cooled to 0° C. 4.13 g (20 mmol) of N,N'-dicyclohexylcarbodiimide is added and stirred for 30 minutes at 0° C., then for 2 hours at room temperature. It is cooled to 0° C., and 10 g (10.76 mmol) of the title compound of Example 25b) is added, then 4.05 g (40 mmol) of triethylamine, and it is allowed to come slowly to room temperature (about 4 hours). It is evaporated to the dry state in a vacuum, the residue is taken up in 400 ml of methylene chloride, and urea is filtered out. The filtrate is extracted three times with an aqueous hydrochloric acid (pH 3.0, 600 ml each), dried on magnesium sulfate and evaporated to the dry state. The residue is chromatographed on silica gel (mobile solvent: methylene chloride/methanol=20:1, (+2% acetic acid)).

Yield: 14.22 g (91% of theory) of a colorless solid
Elementary analysis:
Cld: C, 50.45; H, 5.14; N, 8.68; F, 17.01; S, 2.21;
Fnd: C, 50.27; H, 5.31; N, 8.49; F, 16.83; S, 2.07;

d) 1,4,7-Tris[N-(2-amino)-acetyl]-10-N-{undecanoyl-<11-amino-N-[acetyl-(2-amino-N-ethyl-N-perfluorooctylsulfonyl)]>}-1,4,7,10-tetraazacyclododecane, trihydrobromide 10 g (6.89 mmol) of the title compound of Example 25c) is dissolved in 100 ml of acetic acid and added in drops to a solution of 200 ml of hydrogen bromide in glacial acetic acid (33%) whose temperature is 60° C. It is stirred for 1 hour at 60° C. It is cooled to 0° C., and 2,000 ml of diethyl ether is slowly added in drops while being stirred. The deposited precipitate is filtered off, rewashed twice with 200 ml of ether and dried in a vacuum furnace (60° C.).

Yield: 8.93 g (97% of theory) of a cream-colored, crystalline solid
Elementary analysis:
Cld: C, 33.25; H, 4.45; N, 9.43; F, 24.16; S, 2.40; Br, 17.93;
Fnd: C, 33.07; H, 4.68; N, 9.30; F, 24.03; S, 2.17; Br, 17.68;

e) 1,4,7-Tris{N-[3,9-bis(N-t-butyloxycarbonylmethyl)]-6-[N-(3-aza-2,5-dioxo-pentane)-1,5-diyl]-3,6,9-triazaundecane-1,11-dioic acid-di-t-butyl ester}-10-N-{undecanoyl-<11-amino-N-[acetyl-(2-amino-N-ethyl-N-perfluorooctylsulfonyl)]>}-1,4,7,10-tetraazacyclododecane 10.21 g (88.7 mmol) of N-hydroxysuccinimide and 18.30 g (88.7 mmol) of N,N'-dicyclohexylcarbodiimide are added to 27.35 g (44.35 mmol) of sym-DTPA-tetra-tert-butyl ester, dissolved in 400 ml of dimethylformamide, at 0° C., and it is stirred for one hour at this temperature. Then, it is stirred for 3 hours at room temperature. 9.88 g (7.39 mmol) of the title compound of Example 25d) and 17.91 g (177 mmol) of triethylamine are added to this solution. It is stirred for 24 hours at room temperature. The solution is evaporated to the dry state, and the residue is taken up in 400 ml of dichloromethane. Dicyclohexylurea is filtered out, and the filtrate is washed twice with 200 ml of 5% aqueous sodium carbonate solution. The organic phase is dried on magnesium sulfate and evaporated to the dry state in a vacuum. The residue is chromatographed on silica gel (mobile solvent: dichloromethane/methanol=20:1).

Yield: 19.67 g (92% of theory) of a colorless, viscous oil

Elementary analysis:

Cld: C, 52.72; H, 7.49; N, 8.71; F, 11.16; S, 1.11;

Fnd: C, 52.60; H, 7.62; N, 8.60; F, 11.01; S, 1.04;

f) 1,4,7-Tris{N-[3,9-bis(N-carboxylatomethyl)]-6-[N-(3-aza-2,5-dioxo-pentane)-1,5-diyl]-3,6,9-triazaundecane-1-carboxylato-11-acid, Gd complex, monosodium salt}-10-N-{undecanoyl-<11-amino-N-[acetyl-(2-amino-N-ethyl-N-perfluorooctyl-sulfonyl)]>}-1,4,7,10-tetraazacyclododecane 10.53 g (3.64 mmol) of the title compound of Example 25e) is dissolved in 200 ml of trifluoroacetic acid and stirred for 12 hours at room temperature. It is evaporated to the dry state in a vacuum. The residue is dissolved in 200 ml of water and set at pH 4 with 10% aqueous sodium hydroxide solution. Then, 1.98 g (5.46 mmol) of gadolinium oxide is added, and it is stirred for 2 hours at 70° C. It is cooled to room temperature and set at pH 7.2 with 10% aqueous sodium hydroxide solution. The solution is mixed with 3 g of activated carbon, stirred for 1 hour at room temperature and filtered. The filtrate is filled in an ultrafiltration cell and dialyzed (AMICON® YM-1 (cut-off 1,000 Da)). Dialysis is performed until the eluate has reached a conductivity of 10 μS. Then, the contents of the ultrafiltration cell are freeze-dried.

Yield: 9.50 g (95% of theory) of a colorless, amorphous powder

Water content: 7.5%

Elementary analysis (relative to anhydrous substance):

Cld: C, 34.52; H, 3.92; N, 9.17; F, 11.75; S, 1.17; Gd, 17.16; Na, 2.51;

Fnd: C, 34.37; H, 4.08; N, 9.09; F, 11.69; S, 1.08; Gd, 17.05; Na, 2.33;

EXAMPLE 26 a) 1,4,7-Tris{N-2,6-[bis(benzyloxycarbonylamino)]-hexanoyl}-10-N-[acetyl-(2-amino-N-ethyl-N-perfluorooctylsulfonyl)]}-1,4,7,10-tetraazacyclododecane 5.46 g (7.39 mmol) of the title compound of Example 12d) and 15.33 g (37 mmol) of di-Z-lysine are dissolved in 150 ml of dimethylformamide, and 11.13 g (45 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: dichloromethane/acetone=25:1).

Yield: 11.12 g (78% of theory) of a colorless, viscous oil

Elementary analysis:

Cld: C, 53.55; H, 5.12; N, 7.99; F, 16.74; S, 1.66;

Fnd: C, 53.37; H, 5.31; N, 7.82; F, 16.55; S, 1.49;

b) 1,4,7-Tris{[N-(2,6-diamino)-hexanoyl]-10-[N-acetyl-(2-amino-N-ethyl-N-perfluorooctylsulfonyl)]}-1,4,7,10-tetraazacyclododecane 8.27 g (4.29 mmol) of the title compound of Example 26a) is dissolved in 80 ml of acetic acid and added in drops to a solution of 150 ml of hydrogen bromide in glacial acetic acid (33%) whose temperature is 60° C. It is stirred for 1 hour at 60° C. It is cooled to 0° C., and 600 ml of diethyl ether is slowly added in drops while being stirred. The deposited precipitate is filtered off, rewashed twice with 200 ml of ether and dried in a vacuum furnace (60° C.).

Yield: 6.56 g (95% of theory) of a cream-colored, crystalline solid

Elementary analysis:

Cld: C, 28.36; H, 4.26; N, 9.57; F, 20.07; S, 1.99; Br, 29.79;

Fnd: C, 28.17; H, 4.41; N, 9.41; F, 19.92; S, 1.85; Br, 29.45;

c) 1,4,7-Tris{N-hexanoyl-2,6-bis<amino-N-acetyl-2-[3,9-bis(N-t-butyloxy-carbonyl-methyl)-6-yl-3,6,9-triaazaundecane-1,11-dicarboxylic acid-di-t-butyl ester]>}-10-[N-acetyl-(2-amino-N-ethyl-N-perfluorooctylsulfonyl)]}-1,4,7,10-tetraazacyclododecane 20.42 g (177.4 mmol) of N-hydroxysuccinimide and 36.6 g (177.4 mmol) of N,N'-dicyclohexylcarbodiimide are added to 54.7 g (88.7 mmol) of sym-DTPA-tetra-tert-butyl ester, dissolved in 500 ml of dimethylformamide, at 0° C., and it is stirred for one hour at this temperature. Then, it is stirred for 3 hours at room temperature. 11.89 g (7.39 mmol) of the title compound of Example 26b) and 35.42 g (350 mmol) of triethylamine are added to this solution. It is stirred for 24 hours at room temperature. The solution is evaporated to the dry state, and the residue is taken up in 800 ml of dichloromethane. Dicyclohexylurea is filtered out, and the filtrate is washed twice with 400 ml of 5% aqueous sodium carbonate solution. The organic phase is dried on magnesium sulfate and evaporated to the dry state in a vacuum. The residue is chromatographed on silica gel (mobile solvent: dichloromethane/methanol=20:1).

Yield: 30.68 g (92% of theory) of a colorless, viscous oil

Elementary analysis:

Cld: C, 53.23; H, 8.62; N, 9.00; F, 7.16; S, 0.71;

Fnd: C, 53.05; H, 8.84; N, 8.81; F, 7.03; S, 0.65;

d) 1,4,7-Tris{N-hexanoyl-2,6-bis<amino-N-acetyl-2-[3,9-bis(N-carboxylato-methyl)-6-yl-3,6,9-triazaundecane-1-carboxylato-11-acid, Gd complex, monosodium salt]>}-10-[N-acetyl-(2-amino-N-ethyl-N-perfluorooctylsulfonyl)]-1,4,7,10-tetraazacyclododecane 16.43 g (3.64 mmol) of the title compound of Example 26c) is dissolved in 300 ml of trifluoroacetic acid, and it is stirred for 12 hours at room temperature. It is evaporated to the dry state in a vacuum. The residue is dissolved in 200 ml of water and set at pH 4 with 10% aqueous sodium hydroxide solution. Then, 3.96 g (10.92 mmol) of gadolinium oxide is added, and it is stirred for 2 hours at 70° C. It is cooled to room temperature and set at pH 7.2 with 10% aqueous sodium hydroxide solution. The solution is mixed with 3 g of activated carbon, stirred for 1 hour at room temperature and filtered. The filtrate is filled in an ultrafiltration cell and dialyzed (AMICON® YM-1 (cut-off 1,000 Da)). Then, the contents of the ultrafiltration cell are freeze-dried.

Yield: 14.76 g (96% of theory) of a colorless, amorphous powder

Water content: 9.5%

Elementary analysis (relative to anhydrous substance):

Cld: C, 29.58; H, 4.06; N, 9.62; F, 7.65; S, 0.76; Gd, 22.34; Na, 3.27;

Fnd: C, 29.39; H, 4.24; N, 9.43; F, 7.48; S, 0.69; Gd, 22.17; Na, 3.11;

EXAMPLE 27

1,4,7-Tris{N-hexanoyl-2,6-bis<amino-N-acetyl-2-[aminopropanoyl-(2-yl)]-[1,4,7-tris(N-carboxylatomethyl)- 1,4,7,10-tetraazacyclododecan-10-yl, Gd complex]>}-10-[N-acetyl-(2-amino-N-ethyl-N-perfluorooctylsulfonyl)]-1,4,7,10-tetraazacyclododecane 28.97 g (46 mmol) of the Gd complex, described in Example 1f), of 10-(4-carboxy-1-methyl-2-oxo-3-azabutyl)-1,4,7,10-tetraazacyclododecane-1,4,7-triacetic acid, 4.7 g of sodium bromide (46 mmol) and 10.59 g (92 mmol) of N-hydroxysuccinimide are dissolved in 300 ml of dimethyl sulfoxide at 50° C. After cooling to room temperature, 18.98 g (92 mmol) of N,N'-dicyclohexylcarbodiimide is added and preactivated for 60 minutes. A solution of 6.16 g (3.83 mmol) of the title compound that is described in Example 26b) and 20.34 g (200 mmol) of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-1 ultrafiltration membrane (cut-off 1,000 Da), and low-molecular components are removed. The retentate is then freeze-dried.

Yield: 16.15 g (92% of theory)

$H_2O$ content: 11.3%

Elementary analysis (relative to anhydrous substance):

Cld: C, 35.11; H, 5.19; N, 12.53; S, 0.70; F, 7.05; Gd, 20.58;

Fnd: C, 35.01; H, 5.32; N, 11.27; S, 0.64; F, 6.91; Gd, 20.39;

TABLE 1

Determination of the $T^1$-Relaxivity of Selected Compounds
The relaxivity of the following compounds was determined with a Minispec pc 20 (20 MHz, 0.47 T) at 37° C. in human plasma and compared to that of Gd-DTPA-polylysine and Magnevist(R) as comparison substances. Since the substances according to the invention contain more than one metal atom, the relaxivity was normalized to one metal atom for purposes of comparison.

| Substance Example No. | $R^1$ [L/mmol*sec] at 0.47 T and 37° C. |
|---|---|
| 14e) | 19.3 |
| 8b) | 20.6 |
| 18d) | 23.0 |

TABLE 1-continued

Determination of the $T^1$-Relaxivity of Selected Compounds
The relaxivity of the following compounds was determined with a Minispec pc 20 (20 MHz, 0.47 T) at 37° C. in human plasma and compared to that of Gd-DTPA-polylysine and Magnevist(R) as comparison substances. Since the substances according to the invention contain more than one metal atom, the relaxivity was normalized to one metal atom for purposes of comparison.

| Substance Example No. | $R^1$ [L/mmol*sec] at 0.47 T and 37° C. |
|---|---|
| 19 | 21.4 |
| 25f) | 15.1 |
| 1g) | 19.5 |
| 26d) | 13.0 |
| 27 | 16.1 |
| Magnevist(R) | 4.8 |
| Gd-DTPA-polylysine | 16.8 |

EXAMPLE 28

Lymph Node Concentration in Guinea Pigs

The gadolinium complex of Example 19 was studied 30 minutes/90 minutes after subcutaneous administration (10 µmol of total gadolinium/kg of body weight, hind paw s.c.) to stimulated guinea pigs (complete Freund adjuvant; in each case 0.1 ml in the right and left upper and lower legs; 2 weeks before administration of the test substance) to determine their lymph node concentration in three successive lymph node stations (popliteal, inguinal, iliac). In this case, the results that are listed below (determination of gadolinium concentration using ICP-AES) are obtained:

Gd-Concentration [µmol/l] in three successive lymph node stations 30 and 90 minutes after interstitial administration of 10 µmol/kg (MW±SD, n=3)

| | Gd Concentration in [µmol/l] | |
|---|---|---|
| Lymph Nodes | 30 minutes p.i. | 90 minutes p.i. |
| popliteal | 345 ± 319 | 75 ± 20 |
| inguinal profund | 43 ± 41 | 9 ± 2 |
| iliac | 50 ± 18 | 20 ± 8 |
| blood | 24 ± 3 | 25 ± 4 |
| urine | 261 ± 167 | 348 ± 119 |

At the same dose, the lymph-node accumulations that are achieved with this invention exceed the accumulations that are achieved with an extracellular contrast medium (Gd-DTPA) by a factor of 5–7.

EXAMPLE 29

Retention of the Opacifying Metal at the Injection Site

After s.c. administration of 10 µmol of total gadolinium (Example 19)/kg of body weight in the guinea pig's paw, the retention of metal at the injection site was studied at different times.

Gd-Concentration [% dose] at the Administration Site (Paw), After Interstitial Administration of 10 µmol/kg (MW±SD, n=3)

| Substance | Gadolinium Concentration at the injection site (paw) [% of dose] | | |
|---|---|---|---|
| | 30 minutes p.i. | 90 minutes p.i. | 7 days p.i. |
| Example 19 | 48.4 ± 10.4% | 8.0 ± 1.7% | 0.7 ± 0.6% |

EXAMPLE 30

Elimination of the Contrast Medium after S.C. Administration

After subcutaneous administration of 10 μmol of total gadolinium (Example 19)/kg of body weight in the hind paw of the guinea pig, the retention of metal in the liver, in the kidneys and in the spleen was examined 7 days after administration.
Gd Concentration [% of Dose] in the Liver, Kidneys, Spleen (7 d p.i.) After Interstitial Administration of 10 μmol/kg (MW±SD, n=2)

| Substance | Gadolinium Content in the Organs 7 d p.i. [% dose] | | |
|---|---|---|---|
| | Liver | Kidneys | Spleen |
| Example 19 | 0.09 ± 0.09% | 0.06 ± 0.04% | 0.00 ± 0.01% |

EXAMPLE 31

Example of an In-Vivo Comparison with an Intravascular and an Extracellular Contrast Medium in Blocked Kidneys (Diffusibility) in Rats The suitability of the compound that is described in Example 1 g as a blood-pool agent is shown in the following test.

As test animals, three 250 g male (Schering-SPF) rats were used. The renal vessels in the animals were blocked to prevent renal elimination and, assuming that fecal elimination is negligible, to obtain a measure of the diffusibility of the formulation according to the invention from the blood into the surrounding tissue. 0.5 ml (in each case 10 mmol/l) of the following contrast medium solution was intravenously administered per animal: a mixture consisting of 1 part each of the compound of Example 1g, named compound 1 below, of intravascular contrast medium Eu-DTPA-albumin, named compound 2 below and of extracellular contrast medium Dy-DTPA, named compound 3 below. Via a catheter in the common carotid artery, blood samples were taken at the following times: 15, 30, 45, 60, 90 seconds; 3, 5, 10, 15 minutes p.i. In the blood samples that were obtained, in each case the concentrations of gadolinium (Gd), europium (Eu) and dysprosium (Dy) were measured in parallel using atom emission spectrometry (ICP-AES). The proportion of the intravascular contrast medium compound 2 (Eu) that remains in the blood space was set at 100%. It was possible to compare the proportion of the formulation according to the invention of compound 1 (Gd) and compound 3 (Dy, extracellular comparison substance) that remained in the blood space by the different labeling in the same animal, and the proportion was set as a percentage of the concentration of compound 2. These data thus provide information on the compounds remaining in the intravascular space.

Results: FIG. 1 shows the blood level (in μmol/l) of the formulation according to the invention in comparison to Eu-DTPA-BSA and Dy-DTPA (in each case 20 μmol/kg) in rats. The diffusion of the formulation according to the invention (compound 1) in the interstice was only slightly faster in comparison to Eu-DTPA-BSA (compound 2) in the first minute p.i., but significantly increased during the rest of the test. In comparison to Dy-DTPA (compound 3), it was slower during the entire test period. significantly higher blood concentrations of compound 1 compared with the extracellular contrast medium (compound 2) were obtained mainly at the early times.

The diffusibility of the formulation according to the invention (compound 1) from the vascular space into the surrounding tissue is higher than the "pure" intravascular contrast medium (compound 2), but significantly lower compared to the free diffusible, extracellular compound 3 (see Table 2). This diffusibility test illustrates the special suitability of the formulation according to the invention as a blood-pool contrast medium for diagnostic visualization of the vessels or pathological vascular changes (angiography).

TABLE 2

| Percentage of the dose that remains in the blood space. | | | |
|---|---|---|---|
| | 30 seconds | 3 minutes | 10 minutes |
| Eu (compound 2) | 100% | 100% | 100% |
| Gd (compound 1) | 84% | 62% | 44% |
| Dy (compound 3) | 48% | 25% | 21% |

EXAMPLE 32

Blood Elimination Kinetics

The blood-elimination kinetics of the compound of Example 1g was examined in rats (Han. Wistar, Schering SPF, ≈250 g of body weight). For this purpose, after one-time intravenous administration (via a caudal vein) of the substances (dose: ≈100 μmol of metal per kg of body weight), the substance concentration in the blood (based on the Gd or Dy content) was determined over a period of up to 120 minutes p.i. using ICP-AES. The pharmacokinetic parameters: distribution volume (Vss), total clearance (CLtot) and elimination half-life (tb) were calculated with a special computer program (TOPFIT 2.0; Thomae, Schering, Gödecke), whereby a two-compartment distribution model was used as a basis.

FIG. 2 shows the elimination from the blood (in % of the injected dose) of Dy-DTPA (dose; 101 μmol of Dy per kg of body weight, n=3) and the compound of Example 1g (dose: 96 μmol of Gd per kg of body weight, n=3) after one-time intravenous administration of the substances in rats (Han Wistar, Schering SPF, ≈250 g of body weight).

The Gd and Dy contents in the blood were determined using ICP-AES.

In comparison to Dy-DTPA (the dysprosium analog of Magnevist®, the compound of Example 1g showed a significantly slower elimination from the blood and, in addition, a smaller distribution volume. It has therefore been determined that this compound, surprisingly enough, has an extended retention in the blood space and therefore should be suitable as a "blood-pool contrast medium," e.g. for visualizing blood vessels with suitable techniques, and based on the surprisingly high relaxivity ($r_{1,plasm} \approx 19.5$ [$l \cdot mmol^{-1} \cdot s^{-1}$]) here also at relatively small doses of $\leq 50$ μmol of Gd per kg of body weight.

TABLE 3

Pharmacokinetic Parameters: Distribution Volume (Vss),
Total Clearance (CLtot) and Elimination Half-Life (tβ) of Dy-DTPA
and Example 1g.
(Calculated with TOPFIT 2.0; two-compartment model).

| | Vss (l/kg) | | CLtot {mU (min*kg)} | | tα$^{(min)}$ | | tβ$^{(min)}$ | |
|---|---|---|---|---|---|---|---|---|
| | MEAN | SD | MEAN | SD | MEAN | SD | MEAN | SD |
| Dy-DTPA | 0.17 | 0.03 | 6.75 | 1.31 | 2.07 | 0.46 | 20.7 | 3.9 |
| Example 1g | 0.09 | 0.01 | 0.41 | 0.08 | 4.06 | 0.80 | 168.8 | 49.3 |

EXAMPLE 33

Blood-Elimination Kinetics

The blood-elimination kinetics of the compound of Example 19 was examined in rats (Han. Wistar, Schering SPF, ≈250 g of body weight). For this purpose, after one-time intravenous administration (via a caudal vein) of the substances (dose: ≈100 μmol of metal per kg of body weight), the substance concentration in the blood (based on the metal content) was determined over a period of up to 120 minutes p.i. using ICP-AES. The pharmacokinetic parameters: distribution volume (Vss), total clearance (CLtot) and elimination half-life (tb) were calculated with a special computer program (TOPFIT 2.0; Thomae, Schering, G ödecke), whereby a two-compartment distribution model was used as a basis.

FIG. 3 shows the elimination from the blood (in % of the injected dose) of Dy-DTPA (dose: 101 μmol of Dy per kg of body weight, n=3) and the compound of Example 19 (dose: 96 μmol of Gd per kg of body weight, n=3) after one-time intravenous administration of the substances in rats (Han Wistar, Schering SPF, ≈250 g of body weight).

The Gd and Dy contents in the blood were determined using ICP-AES.

In comparison to Dy-DTPA (the dysprosium analog of Magnevist®, the compound of Example 19 showed a significantly slower elimination from the blood and, in addition, a smaller distribution volume. It has therefore been determined that this compound, surprisingly enough, has an extended retention in the blood space and therefore should be suitable as a "blood-pool contrast medium," e.g., for visualizing blood vessels with suitable techniques, and based on the surprisingly high relaxivity ($r_{1,plasm}$≈19.5 [l*mmol$^{-1}$*s$^{-1}$]) here also at relatively small doses of ≦50 μmol of Gd per kg of body weight.

EXAMPLE 34

Contrast-Medium-Supported MR Angiography

The studies on contrast-medium-supported MR angiography were performed on an experimental MRT system (SISCO SIS 85, 2.0 tesla) with a 3 D FLASH technique (10/2.6/40°).

To determine the effectiveness of contrast media for visualizing blood vessels, anesthetized (Rompun®+ Ketavet®, 1+1, v/v; ≈1 ml per kg of body weight, i.m.) rats (Han. Wistar; ≈200 g of body weight) were studied by MR tomography.

FIG. 4 shows the pictures of this experiment. The MIP (maximum intensity projection) images were calculated from the 3 D FLASH experiments before (left) and directly after one-time i.v. administration of 50 μmol/kg (center) or 100 μmol/kg (right) of the substance of Example 1g.

Before the administration of contrast media, no blood vessels whatsoever were to be detected (left). After one-time intravenous administration, a pronounced signal increase in the blood vessels and considerable contrasting were detected in the normal tissue (center and right). It was possible to note a pronounced signal increase in the blood vessels after administration, which made possible the visualization of a considerable number of blood vessels.

We claim:

1. Oligomeric compounds that contain perfluoroalkyl of general formula I:

$$A—R^F \qquad (I)$$

in which

A is a molecule portion that contains 2–6 metal complexes that are connected directly or via a linker to a nitrogen atom of an annular skeleton chain, and $R^F$ is a perfluorinated, straight-chain or branched carbon chain with formula $—C_nF_{2n}E$, in which E represents a

TABLE 4

Pharmacokinetic Parameters: Distribution Volume (Vss),
Total Clearance (CLtot) and Elimination Half-Life (tβ) of Dy-DTPA
and of Example 1g.
(Calculated with TOPFIT 2.0; two-compartment model).

| | Vss (l/kg) | | CLtot {ml (min*kg)} | | tα$^{(min)}$ | | tβ$^{(min)}$ | |
|---|---|---|---|---|---|---|---|---|
| | MEAN | SD | MEAN | SD | MEAN | SD | MEAN | SD |
| Dy-DTPA | 0.17 | 0.01 | 6.90 | 0.31 | 1.48 | 0.27 | 18.5 | 0.6 |
| Example 19 | 0.12 | 0.01 | 0.94 | 0.06 | 2.52 | 0.29 | 89.2 | 9.6 | terminal fluorine, chlorine, bromine, iodine, or hydrogen atom and n stands for numbers 4–30,
wherein molecule portion A has the following structure:

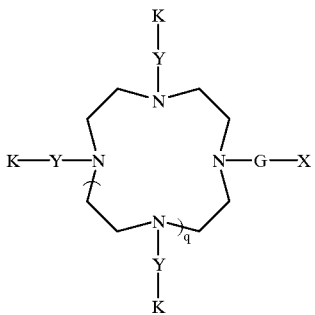

whereby
q is a number 0, 1, 2 or 3,
K stands for a complexing agent or metal complex or their salts of organic and/or inorganic bases or amino acids or amino acid amides,
X is a direct bond to the perfluoroalkyl group, a phenylene group, or a $C_1$–$C_{10}$ alkylene chain, which optionally contains 1–15 oxygen atoms, 1–5 sulfur atoms, 1–10 carbonyl groups, 1–10 (NR) groups, 1–2 $NRSO_2$ groups, 1–10 CONR groups, 1 piperidine group, 1–3 $SO_2$ groups, 1–2 phenylene groups or optionally is substituted by 1–3 radicals $R^F$, in which R stands for a hydrogen atom, a phenyl, benzyl or a $C_1$–$C_{15}$ alkyl group, which optionally contains 1–2 NHCO groups, 1–2 CO groups, 1–5 oxygen atoms, and optionally is substituted by 1–5 hydroxy radicals, 1–5 methoxy radicals, 1–3 carboxy radicals, 1–3 $R^F$ radicals,
Y is a direct bond or a chain of general formula II or III:

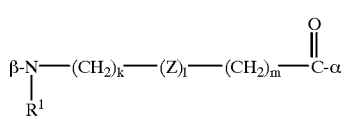

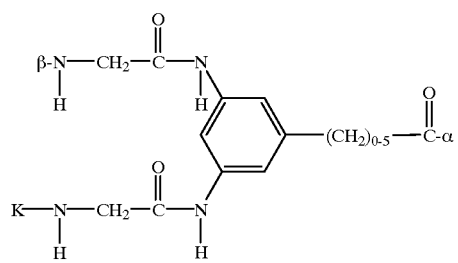

in which
$R^1$ is a hydrogen atom, a phenyl group, a benzyl group or a $C_1$–$C_7$ alkyl group, which optionally is substituted with a carboxy group, a methoxy group, or a hydroxy group,
Z is a direct bond, a polyglycol ether group with 1 to 5 glycol units, or a molecule portion of general formula IV

—CH($R^2$)— (IV)

in which $R^2$ is a $C_1$–$C_7$ carboxylic acid, a phenyl group, a benzyl group, or a —$(CH_2)_{1-5}$—NH—K group, α represents the bond to the nitrogen atom of the skeleton chain, and β is the bond to the complexing agent or metal complex K,
and in which variables k and m stand for natural numbers between 0 and 10 and 1 stands for 0 or 1,
and whereby
G is a CO or $SO_2$ group.

2. Compounds according to claim 1, wherein q is the number 1.

3. ompounds according to claim 1, wherein molecule portion X is an alkylene chain, which contains 1–10 $CH_2CH_2O$ groups or 1–5 $COCH_2NH$ groups.

4. Compounds according to claim 1, wherein molecule portion X is a direct bond or has one of the following structures:

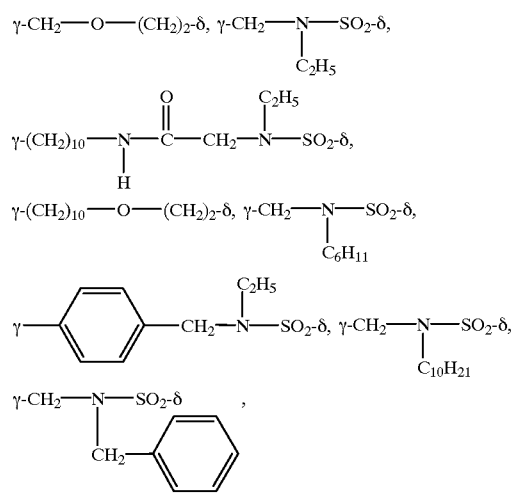

whereby
γ binds to G and δ binds to $R^F$.

5. Compounds according to the claim 1, wherein Y is a molecule portion with one of the following structures:

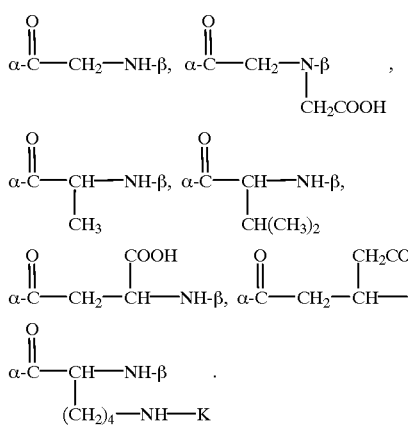

6. Compounds according to claim 1, wherein K represents a complex of general formula V, VI, VII or VIII,

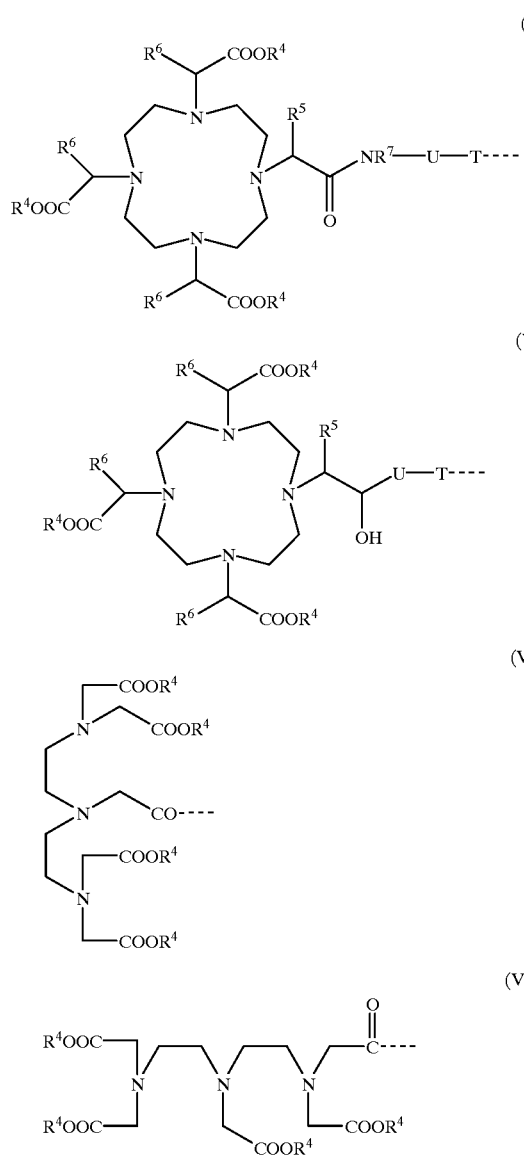

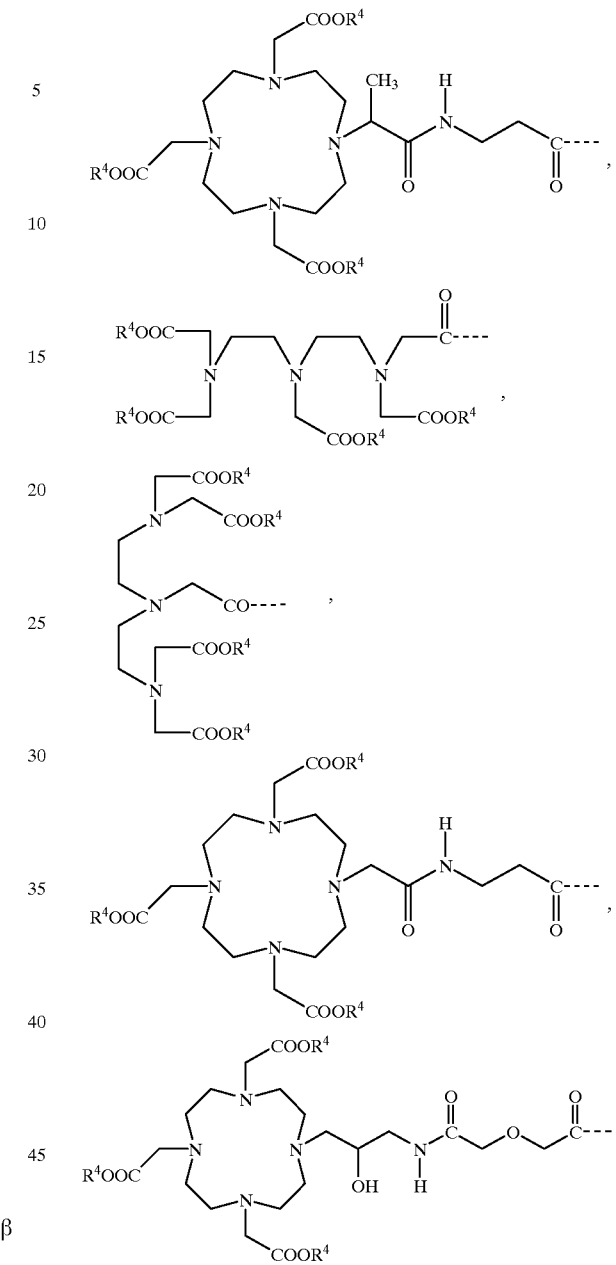

T stands for a —CO—β, —NHCO—β or —NHCS—β group, whereby β represents the binding site to Y.

7. Compounds according to claim 6, wherein the $C_1$–$C_{20}$ alkylene chain that stands for U contains the groups —$CH_2NHCO$—, —$NHCOCH_2O$—, —$NHCOCH_2OC_6H_4$—, —$N(CH_2CO_2H)$—, —$CH_2OCH_2$—, —$NHCOCH_2C_6H_4$—, —$NHCSNHC_6H_4$—, —$CH_2OC_6H_4$—, —$CH_2CH_2O$—, and/or is substituted by the groups —COOH, —$CH_2COOH$.

8. Compounds according to claim 6, wherein U stands for a —$CH_2$—, —$CH_2CH_2$—, —$CH_2CH_2CH_2$—, —$C_6H_4$—, —$C_6H_{10}$—, —$CH_2C_6H_4$—, —$CH_2NHCOCH_2CH(CH_2CO_2H)$—$C_6H_4$—, —$CH_2NHCOCH_2OCH_2$—, —$CH_2NHCOCH_2C_6H_4$ group.

9. Compounds according to claim 1, wherein K has one of the following structures:

wherein $R^4$, independently of one another, are a hydrogen atom or a metal ion equivalent of the elements of atomic numbers 20–32, 37–39, 42–44, 49 or 57–83.

10. Compounds according to claim 1, wherein perfluoroalkyl chain $R^F$ is —$C_6F_{13}$, —$C_8F_{17}$, —$C_{10}F_{21}$ or —$C_{12}F_{25}$.

11. Process for the production of compounds that contain perfluoroalkyl of general formula I according to claim 1, wherein compounds of general formula I'

$$A'—R^F \qquad (I')$$

in which A' stands for a radical

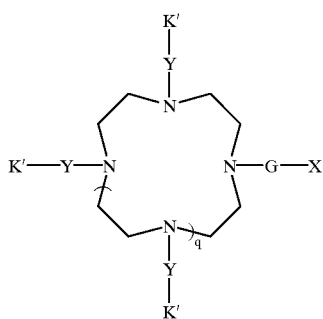

whereby

R⁴, independently of one another, are a hydrogen atom or a metal ion equivalent of the elements of atomic numbers 20–32, 37–39, 42–44, 49 or 57–83, R⁵ is a hydrogen atom or a straight-chain, branched, saturated or unsaturated $C_1$–$C_{30}$ alkyl chain, which optionally is substituted by 1–5 hydroxy groups, 1–3 carboxy groups or 1 phenyl group(s) and/or optionally is interrupted by 1–10 oxygen atoms, 1 phenylene or 1 phenylenoxy group, R⁶ is a hydrogen atom, a straight-chain or branched $C_1$–$C_7$ alkyl radical, a phenyl or benzyl radical, R⁷ is a hydrogen atom, a methyl or ethyl group, which optionally is substituted by a hydroxy or carboxy group, U is a straight-chain, branched, saturated or unsaturated $C_1$–$C_{20}$ alkylene group that optionally contains 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atoms, and/or optionally is substituted by 1–5 hydroxy, 1–2 mercapto, 1–5 oxo, 1–5 thioxo, 1–3 carboxy, 1–5 carboxyalkyl, 1–5 ester and/or 1–3 amino groups, whereby the optionally contained phenylene groups can be substituted by 1–2 carboxy, 1–2 sulfone or 1–2 hydroxy groups, and K' stands for K with R⁴ in the meaning of a hydrogen atom or a carboxy protective group, are reacted after cleavage of the optionally present protective groups in a way that is known in the art with at least one metal oxide or metal salt of an element of atomic numbers 20–32, 37–39, 42–44, 49 or 57–83 and optionally then still present acidic hydrogen atoms in the complex compounds that are thus obtained are substituted completely or partially by cations of inorganic and/or organic bases, amino acids or amino acid amides.

12. Process for the production of compounds that contain perfluoroalkyl of general formula I according to claim 1, wherein a compound of general formula I"

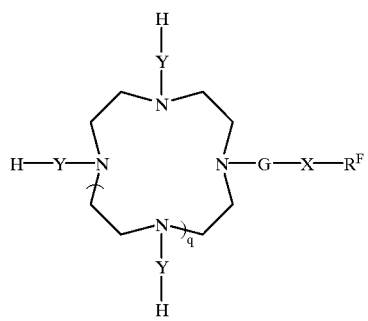

is reacted with a complex V' or VI',

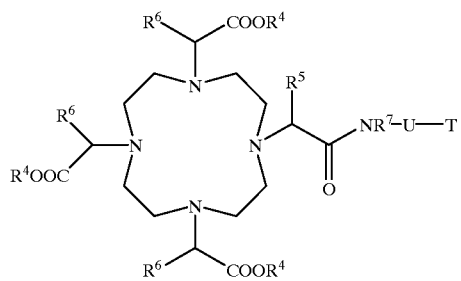

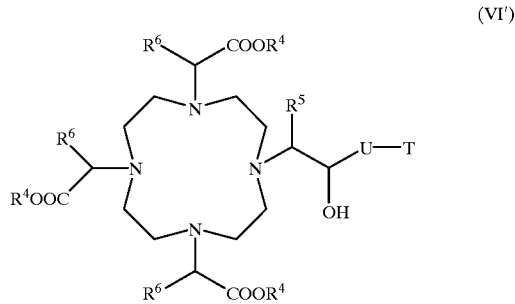

whereby T' stands for a —C*O, —COOH, —N=C=O or —N=C=S group and —C*O stands for an activated carboxyl group, provided that at least two (in the case of divalent metals) or three (in the case of trivalent metals) of substituents R⁴ stand for a metal ion equivalent of the above-mentioned elements, and that optionally other carboxyl groups are present in the form of their salts with inorganic and/or organic bases, amino acids or amino acid amides.

13. Pharmaceutical agents that contain at least one physiologically compatible compound according to claim 1, optionally with the additives that are commonly used in galenicals.

14. Process for the production of pharmaceutical agents according to claim 13, wherein the compounds that contain perfluoroalkyl and that are present in water or physiological salt solution, are brought into a form that is suitable for enteral or parenteral administration optionally with the additives that are commonly used in galenicals.

15. A method for ¹H-NMR diagnosis or ¹H-NMR spectroscopy which comprises administering a physiologically compatible composition containing a compound according to claim 1, as a contrast agent, and performing the ¹H-NMR diagnosis or ¹H-NMR spectroscopy.

16. A method for diagnostic radiology which comprises administering a physiologically compatible composition containing a compound according to claim 1, as a contrast agent, and performing the diagnostic radiology.

17. A method for radiodiagnosis or radiotherapy which comprises administering a physiologically compatible composition containing a compound according to claim 1, as a pharmaceutical agent, and performing the radiodiagnosis or radiotherapy.

18. A method for blood pool diagnosis which comprises administering a physiologically compatible composition containing a compound according to claim 1, as a blood pool contrast agent, and performing the blood pool diagnosis.

19. A method for lymphography which comprises administering a physiologically compatible composition containing a compound according to claim 1, as a lymphatic system contrast agent, and performing the lymphography.

20. A pharmaceutical agent according to claim 13, which contains the oligomeric compound in complex form in an amount of 0.1 $\mu$mol to 1 mmol per liter.

* * * * *